United States Patent
Feng et al.

(10) Patent No.: US 10,982,052 B2
(45) Date of Patent: Apr. 20, 2021

(54) SILICONE BLOCK COPOLYMER HAVING AN AMINOFUNCTIONAL ENDBLOCKING GROUP AND METHOD FOR ITS PREPARATION AND USE

(71) Applicant: Dow Silicones Corporation, Midland, MI (US)

(72) Inventors: Qian Feng, Midland, MI (US); Brian Harkness, Midland, MI (US); Kimmai Thi Nguyen, Midland, MI (US); Hannah Schmidt, Auburn, MI (US); Nisaraporn Suthiwangcharoen, Midland, MI (US); Bethany Johnson, Midland, MI (US)

(73) Assignee: Dow Silicones Corporation, Midland, MI (US)

( * ) Notice: Subject to any disclaimer, the term of this patent is extended or adjusted under 35 U.S.C. 154(b) by 292 days.

(21) Appl. No.: 16/077,862

(22) PCT Filed: Apr. 24, 2017

(86) PCT No.: PCT/US2017/029056
§ 371 (c)(1),
(2) Date: Aug. 14, 2018

(87) PCT Pub. No.: WO2017/196524
PCT Pub. Date: Nov. 16, 2017

(65) Prior Publication Data
US 2020/0325280 A1    Oct. 15, 2020

Related U.S. Application Data

(60) Provisional application No. 62/334,060, filed on May 10, 2016.

(51) Int. Cl.
| | | |
|---|---|---|
| *C08G 77/26* | (2006.01) | |
| *C08G 77/50* | (2006.01) | |
| *A61K 8/06* | (2006.01) | |
| *A61K 8/898* | (2006.01) | |
| *A61Q 5/02* | (2006.01) | |
| *A61Q 5/12* | (2006.01) | |
| *C08G 77/44* | (2006.01) | |
| *D06M 15/643* | (2006.01) | |

(52) U.S. Cl.
CPC .............. *C08G 77/50* (2013.01); *A61K 8/062* (2013.01); *A61K 8/898* (2013.01); *A61Q 5/02* (2013.01); *A61Q 5/12* (2013.01); *C08G 77/26* (2013.01); *C08G 77/44* (2013.01); *D06M 15/6436* (2013.01); *A61K 2800/10* (2013.01); *A61K 2800/31* (2013.01); *A61K 2800/48* (2013.01); *A61K 2800/5426* (2013.01)

(58) Field of Classification Search
CPC ........ C08G 77/50; C08G 77/26; C08G 77/12; A61K 8/898
See application file for complete search history.

(56) References Cited

U.S. PATENT DOCUMENTS

| | | | |
|---|---|---|---|
| 2,798,053 | A | 7/1957 | Brown |
| 3,958,581 | A | 5/1976 | Abegg et al. |
| 3,962,418 | A | 6/1976 | Birkofer |
| 4,009,256 | A | 2/1977 | Nowak, Jr. et al. |
| 4,122,029 | A | 10/1978 | Gee et al. |
| 4,661,577 | A * | 4/1987 | Jo Lane ............ D06M 15/6436 |
| | | | 106/18.12 |
| 4,704,272 | A | 11/1987 | Oh et al. |
| 4,741,855 | A | 5/1988 | Grote et al. |
| 4,788,006 | A | 11/1988 | Bolich, Jr. et al. |
| 5,132,443 | A * | 7/1992 | Traver .................. A61K 8/898 |
| | | | 556/425 |
| 5,262,506 | A | 11/1993 | Okawa et al. |
| 5,387,417 | A | 2/1995 | Rentsch |
| 5,442,083 | A * | 8/1995 | Kobayashi ............. C08G 77/50 |
| | | | 556/434 |
| 5,543,074 | A | 8/1996 | Hague et al. |
| 5,583,095 | A * | 12/1996 | Kobayashi ........... C10M 107/00 |
| | | | 508/207 |
| 5,807,956 | A | 9/1998 | Czech |
| 5,811,487 | A | 9/1998 | Schulz, Jr. et al. |
| 5,919,441 | A | 7/1999 | Mendolia et al. |
| 5,981,680 | A | 11/1999 | Petroff et al. |
| 6,013,682 | A | 1/2000 | Dalle et al. |
| 6,051,216 | A | 4/2000 | Barr et al. |
| 6,187,891 | B1 | 2/2001 | Rautschek et al. |
| 6,475,568 | B1 | 11/2002 | Czech |
| 6,916,464 | B2 | 7/2005 | Hansenne et al. |
| 6,958,155 | B2 | 10/2005 | Lu et al. |
| 7,078,026 | B2 | 7/2006 | Ferrari et al. |
| 7,887,786 | B2 | 2/2011 | Tournilhac et al. |

(Continued)

FOREIGN PATENT DOCUMENTS

| | | |
|---|---|---|
| WO | 2003105801 | 12/2003 |
| WO | 2004060101 | 7/2004 |
| WO | 2014121037 | 8/2014 |

OTHER PUBLICATIONS

Search report from corresponding China 201780024571.0 application, dated Sep. 15, 2020.

*Primary Examiner* — Margaret G Moore
(74) *Attorney, Agent, or Firm* — Catherine U. Brown

(57) ABSTRACT

A silicone block copolymer having an aminofunctional endblocking group is useful in personal care applications, particularly hair care. A process for making the silicone block copolymer is also described.

13 Claims, No Drawings

(56) References Cited

U.S. PATENT DOCUMENTS

| | | | |
|---|---|---|---|
| 8,013,097 B2 * | 9/2011 | Kennan | C08G 77/46 528/25 |
| 8,957,009 B2 | 2/2015 | Schubert et al. | |
| 2003/0072730 A1 | 4/2003 | Tournilhac | |
| 2003/0170188 A1 | 9/2003 | Ferrari et al. | |
| 2003/0232030 A1 | 12/2003 | Lu et al. | |
| 2003/0235553 A1 | 12/2003 | Lu et al. | |
| 2004/0180032 A1 | 9/2004 | Manelski et al. | |
| 2004/0223936 A1 | 11/2004 | Fecht et al. | |
| 2006/0120983 A1 | 6/2006 | Blin et al. | |
| 2010/0098648 A1 | 4/2010 | Yu | |

\* cited by examiner

SILICONE BLOCK COPOLYMER HAVING AN AMINOFUNCTIONAL ENDBLOCKING GROUP AND METHOD FOR ITS PREPARATION AND USE

CROSS REFERENCE TO RELATED APPLICATIONS

This application is a U.S. national stage filing under 35 U.S.C. § 371 of PCT Application No. PCT/US2017/029056 filed on 24 Apr. 2017, which claims the benefit of U.S. Provisional Patent Application No. 62/334,060 filed 10 May 2016 under 35 U.S.C. § 119 (e). PCT Application No. PCT/US2017/029056 and U.S. Provisional Patent Application No. 62/334,060 are hereby incorporated by reference.

TECHNICAL FIELD

A silicone block copolymer has an aminofunctional endblocking group, methods of making the copolymer, and use of the copolymer for treating hair, textiles, and/or other fibers are disclosed.

BACKGROUND

Silicones have been used extensively for hair, textile, and other fiber treatments. In particular, various amine functional silicones have been developed and sold commercially under various trade names. Common problems associated with amine functional silicones as textile treatments are their yellowing of textiles from the oxidation of the amine groups and extensive hydrophobic nature of the polydimethylsiloxane chains. Thus, efforts over the years have focused on modifying amine functional silicones by adding hydrophilic groups to the siloxane polymers, e.g., as silicone polyether block copolymers, while altering or reducing the amine content to reduce yellowing.

There are several shortcomings using amine functional silicone polyether copolymers. They may be expensive and/or time consuming to prepare. Their performance, particularly in hair care applications, may be insufficient. There is an industry need for cost effective functional silicone materials for hair care compositions that can provide conditioning and/or styling benefits to hair.

SUMMARY

This invention relates to a silicone block copolymer having an aminofunctional endblocking group, or a quat thereof. Said silicone block copolymer has the average formula:

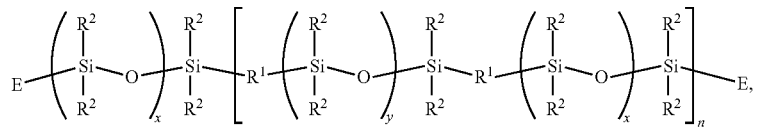

where
  each subscript x is independently >0,
  each subscript y is independently >0,
  subscript n is ≥1,
  each $R^1$ is independently a divalent organic group free of polyoxyalkylene, and
  each $R^2$ is independently a monovalent hydrocarbon group or a monovalent halogenated hydrocarbon group.

In the formula, above, at least one instance of E is an aminofunctional endblocking group, or a quat thereof, where the aminofunctional endblocking group has a formula selected from:

$$-\overset{H_2}{C}\left(\overset{}{\underset{H_2}{C}}\right)_q\overset{R^3}{\underset{}{N}}\left(\overset{}{\underset{H_2}{C}}\right)_r\overset{OH}{\underset{}{CH}}\left(\overset{H_2}{\underset{H_2}{C}}\right)_s\overset{H_2}{\underset{}{C}}-R^{25} \text{ and}$$

$$-\left(\overset{H_2}{\underset{}{C}}\right)_q O\left(\overset{H_2}{\underset{}{C}}\right)_r\overset{H}{\underset{OH}{C}}\left(\overset{H_2}{\underset{}{C}}\right)_s N\overset{R^{23}}{\underset{R^{23}}{-}},$$

where
  subscript q is ≥0,
  subscript r is >0,
  subscript s is ≥0,
  $R^3$ is independently H, an alkyl group, or a group of formula $$-\left(\overset{}{\underset{H_2}{C}}\right)_r\overset{OH}{\underset{}{CH}}\left(\overset{H_2}{\underset{}{C}}\right)_s\overset{H_2}{\underset{}{C}}-R^{25},$$

each $R^{25}$ is independently H or OH, and
  each $R^{23}$ is independently an alkyl group or a hydroxyalkyl group.

This invention also provides a process for preparing the silicone block copolymer with the formula above.

This invention also provides a method of using the silicone block copolymer with the formula above for treatment of substrates such as hair, textiles, and/or other fibers.

DETAILED DESCRIPTION

The silicone block copolymer having an aminofunctional endblocking group, or a quat thereof, has the average formula:

$$E-\left[\left(\overset{R^2}{\underset{R^2}{Si}}-O\right)_x\overset{R^2}{\underset{R^2}{Si}}-R^1\left[\left(\overset{R^2}{\underset{R^2}{Si}}-O\right)_y\overset{R^2}{\underset{R^2}{Si}}-R^1\left(\overset{R^2}{\underset{R^2}{Si}}-O\right)_x\overset{R^2}{\underset{R^2}{Si}}\right]_n\right]-E,$$

where
  each subscript x is independently >0,
  each subscript y is independently >0,
  subscript n is ≥1,
  each $R^1$ is independently a divalent organic group free of polyoxyalkylene, and
  each $R^2$ is independently a monovalent hydrocarbon group or a monovalent halogenated hydrocarbon group, and
  at least one E is an aminofunctional endblocking group, or a quat thereof, where the aminofunctional endblocking group has a formula selected from:

$$-\overset{H_2}{C}\left(\overset{}{\underset{H_2}{C}}\right)_q\overset{R^3}{\underset{}{N}}\left(\overset{}{\underset{H_2}{C}}\right)_r\overset{OH}{\underset{}{CH}}\left(\overset{H_2}{\underset{H_2}{C}}\right)_s\overset{H_2}{\underset{}{C}}-R^{25} \text{ and}$$

-continued $$-\left(\overset{H_2}{\underset{}{C}}\right)_q O\left(\overset{H_2}{\underset{}{C}}\right)_r\overset{H}{\underset{OH}{C}}\left(\overset{H_2}{\underset{}{C}}\right)_s N\overset{R^{23}}{\underset{R^{23}}{-}},$$

where
  subscript q is ≥0,
  subscript r is >0,
  subscript s is ≥0, and
  $R^3$ is independently H, an alkyl group, or a group of formula $$-\left(\overset{}{\underset{H_2}{C}}\right)_r\overset{OH}{\underset{}{CH}}\left(\overset{H_2}{\underset{}{C}}\right)_s\overset{H_2}{\underset{}{C}}-R^{25},$$

each $R^{25}$ is independently H or OH; alternatively OH, and
  each $R^{23}$ is independently an alkyl group or a hydroxyalkyl group.

In the formula above, subscript n is ≥1, alternatively n 1 to 50. Each subscript x is independently >0. Alternatively x may range from 2 to 1,000, alternatively, x may range from 2 to 150, alternatively x may range from 2 to 100, and alternatively x may range from 2 to 50. Each subscript y>0. Alternatively, y may range from 2 to 1,000, alternatively y may range from 100 to 900, alternatively y may range from 200 to 600, and alternatively y may range from 2 to 50. Alternatively, subscript y may have an average value greater than the average value for subscript x. Alternatively, subscripts x, y, and n may have values sufficient that DP of the silicone block copolymer is ≥200, alternatively DP may be 200 to 10,000, alternatively DP may be 400 to 1,000.

In the silicone block copolymer having an aminofunctional endblocking group, the divalent organic groups, designated as $R^1$, link a silicon atom of one organopolysiloxane unit, with another silicon atom in another organopolysiloxane unit in the block copolymer backbone. The divalent organic group $R^1$ is free of polyoxyalkylene groups. "Free of" means containing no polyoxyalkylene groups in $R^1$ groups, (i.e., in the backbone of the silicone block copolymer) or an amount of polyoxyalkylene groups in $R^1$ groups in the backbone undetectable by NMR analysis. The divalent organic group designated as group $R^1$ may be independently selected from divalent hydrocarbon groups containing 2 to 30 carbon atoms, divalent acrylate functional hydrocarbon groups containing 2 to 30 carbon atoms, and/or divalent methacrylate functional hydrocarbon groups containing 2 to 30 carbon atoms. Representative, non-limiting examples of suitable divalent hydrocarbon groups include alkylene groups such as ethylene, propylene (including isopropylene and n-propylene), and butylene (including n-butylene, t-butylene and isobutylene); and pentylene, hexylene, heptylene, octylene, and branched and linear isomers thereof; arylene groups such as phenylene; and alkylarylene groups such as:

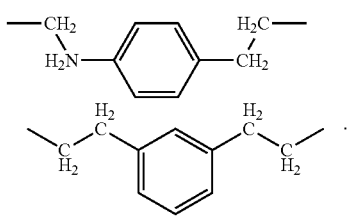

Representative, non-limiting examples of such divalent organofunctional hydrocarbon groups include acrylate-functional alkylene groups and methacrylate-functional alkylene groups. Alternatively, each group $R^1$ may be ethylene, propylene, butylene or hexylene. Alternatively, each instance of group $R^1$ may be ethylene or propylene.

Suitable groups for $R^2$ may be independently selected from monovalent hydrocarbon groups free of aliphatic unsaturation and monovalent halogenated hydrocarbon groups free of aliphatic unsaturation. These monovalent groups may have 1 to 30 carbon atoms, alternatively 1 to 10 carbon atoms, and are exemplified by, but not limited to hydrocarbon groups including alkyl groups such as methyl, ethyl, propyl (including n-propyl and isopropyl), butyl (including n-butyl, t-butyl, sec-butyl and isobutyl), and branched and linear alkyl groups of 5 to 12 carbon atoms including but not limited to pentyl, hexyl, heptyl, octyl, undecyl, and octadecyl (and branched and linear isomers thereof); cycloalkyl such as cyclohexyl; aryl such as phenyl, tolyl, and xylyl; and aralkyl such as benzyl, and 2-phenylethyl; and halogenated hydrocarbon groups such as $CF_3$, fluoromethyl, trifluoroethyl, 2-fluoropropyl, 3,3,3-trifluoropropyl, 4,4,4-trifluorobutyl, 4,4,4,3,3-pentafluorobutyl, 5,5,5,4,4,3,3-heptafluoropentyl, 6,6,6,5,5,4,4,3,3-nonafluorohexyl, and 8,8,8,7,7-pentafluorooctyl; and chlorinated alkyl groups such as chloromethyl and 3-chloropropyl; halogenated carbocyclic groups such as fluorinated cycloalkyl groups such as 2,2-difluorocyclopropyl, 2,3-difluorocyclobutyl, 3,4-difluorocyclohexyl, and 3,4-difluoro-5-methylcycloheptyl; and chlorinated cycloalkyl groups such as 2,2-dichlorocyclopropyl and 2,3-dichlorocyclopentyl. Alternatively, each $R^2$ may be an alkyl group. Alternatively, each $R^2$ may be a methyl group. Alternatively, each $R^2$ may be an alkyl group or an aryl group. Alternatively, each $R^2$ may be a methyl group or a phenyl group.

In the formula, above, at least one instance of E is an aminofunctional endblocking group. Alternatively, both instances of E are aminofunctional endblocking groups. When both instances of E are aminofunctional endblocking groups, they may be the same or different. The aminofunctional endblocking group for E has a formula selected from:

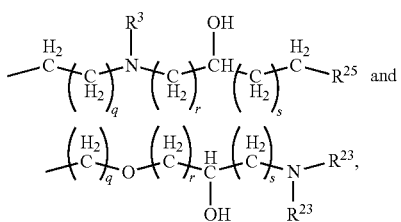

where
subscript q is ≥0,
subscript r is >0,
subscripts is ≥0, $R^3$ is independently H, an alkyl group, or a group of formula

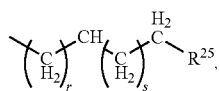

each $R^{25}$ is independently H or OH, and
each $R^{23}$ is independently an alkyl group or a hydroxyalkyl group.

Alternatively, each subscript s may be 0, each $R^{25}$ may be OH, and the group E may have formula:

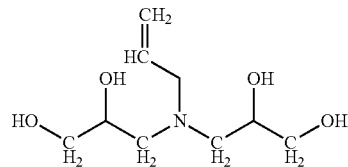

and/or its isomer

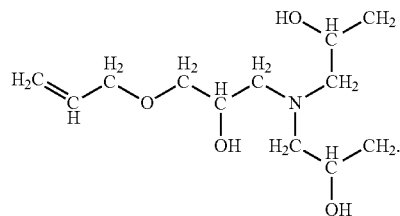

When only one instance of E is aminofunctional, then the other instance of E is a monovalent organic group that is not aminofunctional. The monovalent organic group for the other instance of E may be a monovalent hydrocarbon group or a monovalent halogenated hydrocarbon group as described above for $R^2$. Alternatively, the other instance of E may be a polyoxyalkylene group such as a polyether group. Alternatively, the other instance of E may be an alkyl group, alkenyl group, or a polyether group. Alternatively, the other instance of E may be an alkyl group, such as methyl. In the formulae above, subscript subscript q is ≥0, subscript r is >0, and subscript s is ≥0. Alternatively, subscript q may be 1 to 5, alternatively 1 to 3. Subscript r may be 1 to 5, alternatively 1 to 3. Subscript s may be 1 to 5, alternatively, 1 to 3. Alkyl groups for $R^3$ and $R^{23}$ are as described above for $R^2$, for example, alkyl groups such as methyl, ethyl, propyl (including n-propyl and isopropyl), butyl (including n-butyl, t-butyl, sec-butyl and isobutyl), and branched and linear alkyl groups of 5 to 12 carbon atoms including but not limited to pentyl, hexyl, heptyl, octyl, undecyl, and octadecyl (and branched and linear isomers thereof). Hydroxyalkyl groups for $R^{23}$ are exemplified by any of the alkyl groups where one or more hydrogen atoms is replaced with an OH group. For example, hydroxyalkyl groups include groups of formula $R^{24}OH$, where $R^{24}$ is an alkyl group as described above.

This invention further relates to processes for preparing the silicone block copolymer having an aminofunctional endblocking group described above. A process for preparing said copolymer comprises:

I) reacting ingredients comprising
a) a polyorganosiloxane having an aliphatically unsaturated organic group at each molecular terminal, and
b) a SiH terminated organopolysiloxane,
c) a hydrosilylation catalyst,
where the molar ratio of amount of ingredient b)/amount of ingredient a) is >1, thereby preparing e) an SiH terminated silicone block copolymer of formula

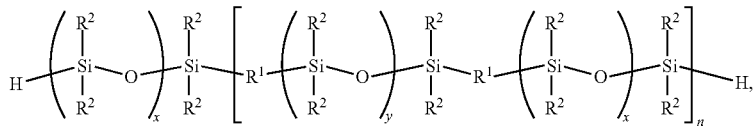

where $R^1$ and $R^2$, and subscripts x, y, and n are as described above;
II) reacting ingredients comprising
a SiH terminated compound selected from ingredient b) the SiH terminated organopolysiloxane, or ingredient e) the SiH terminated silicone block copolymer of formula

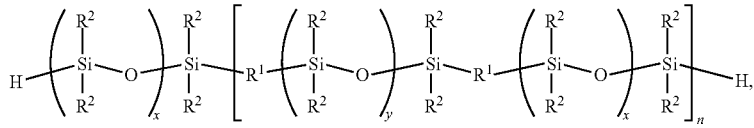

or both ingredient b) and ingredient e), and
f) an epoxide having at least one aliphatically unsaturated hydrocarbon group, thereby forming g) an epoxide functional reaction product;
III) reacting ingredients comprising
g) the epoxide functional reaction product, and
h) an amine compound; thereby forming the silicone block copolymer having aminofunctional endblocking groups, which is described above.

Step I) in the above process involves reacting ingredients comprising a) a polyorganosiloxane having an aliphatically unsaturated organic group at each molecular terminal, b) a SIR terminated organopolysiloxane, and c) a hydrosilylation catalyst. One or more optional ingredients may be added during step I), such as d) a solvent. In step I), the molar ratio of SiH groups on ingredient b) to aliphatically unsaturated hydrocarbon groups on ingredient a) (the "SiH/Vi ratio") is >1.

Ingredient a)
Ingredient a) may comprise a polydiorganosiloxane of formula: $R^6_2R^5SiO(R^6_2SiO)_aSiR^6_2R^5$. In this formula, each $R^5$ is independently an aliphatically unsaturated monovalent organic group and each $R^6$ is independently a monovalent hydrocarbon group free of aliphatic unsaturation or a monovalent halogenated hydrocarbon group free of aliphatic unsaturation. Subscript a is ≥0. Alternatively, subscript a has an average value of at least 2. Alternatively, subscript a may be 2 to 1,000.

The aliphatically unsaturated monovalent organic group may be an aliphatically unsaturated monovalent hydrocarbon group or an aliphatically unsaturated monovalent group that contains heteroatoms. Suitable aliphatically unsaturated monovalent hydrocarbon groups for $R^5$ include alkenyl and alkynyl groups. Suitable alkenyl groups include such as vinyl, allyl, butenyl, and hexenyl. Suitable alkynyl groups include ethynyl and propynyl. Alternatively, suitable aliphatically unsaturated monovalent groups that contain heteroatoms are exemplified by acrylate and/or methacrylate groups, and acrylate functional hydrocarbon groups and/or methacrylate functional hydrocarbon groups.

Suitable groups for $R^6$ may be independently selected from monovalent hydrocarbon groups free of aliphatic unsaturation and monovalent halogenated hydrocarbon groups free of aliphatic unsaturation. These monovalent groups may have from 1 to 30 carbon atoms, alternatively 1 to 10 carbon atoms, and are exemplified by, but not limited to alkyl groups such as methyl, ethyl, propyl (including n-propyl and isopropyl), butyl (including n-butyl, t-butyl, sec-butyl and isobutyl), and branched and linear alkyl groups of 5 to 12 carbon atoms including but not limited to pentyl, hexyl, heptyl, octyl, undecyl, and octadecyl; cycloalkyl such as cyclohexyl; aryl such as phenyl, tolyl, and xylyl; and aralkyl such as benzyl, and 2-phenylethyl; and halogenated hydrocarbon groups such as $CF_3$, fluoromethyl, trifluoroethyl, 2-fluoropropyl, 3,3,3-trifluoropropyl, 4,4,4-trifluorobutyl, 4,4,4,3,3-pentafluorobutyl, 5,5,5,4,4,3,3-heptafluoropentyl, 6,6,6,5,5,4,4,3,3-nonafluorohexyl, and 8,8,8,7,7-pentafluorooctyl; and chlorinated alkyl groups such as chloromethyl and 3-chloropropyl; halogenated carbocyclic groups such as fluorinated cycloalkyl groups such as 2,2-difluorocyclopropyl, 2,3-difluorocyclobutyl, 3,4-difluorocyclohexyl, and 3,4-difluoro-5-methylcycloheptyl; and chlorinated cycloalkyl groups such as 2,2-dichlorocyclopropyl and 2,3-dichlorocyclopentyl. Alternatively, each $R^6$ may be an alkyl group, such as methyl. Alternatively, each $R^6$ may be methyl or phenyl.

Ingredient a) may comprise a polydiorganosiloxane such as
i) dimethylvinylsiloxy-terminated polydimethylsiloxane,
ii) dimethylvinylsiloxy-terminated poly(dimethylsiloxane/methylphenylsiloxane),
iii) dimethylvinylsiloxy-terminated poly(dimethylsiloxane/diphenylsiloxane),
iv) phenyl,methyl,vinyl-siloxy-terminated polydimethylsiloxane,
v) dimethylhexenylsiloxy-terminated polydimethylsiloxane, or
vi) a combination of two or more thereof.

Methods of preparing polydiorganosiloxane fluids suitable for use as ingredient a), such as hydrolysis and condensation of the corresponding organohalosilanes or equilibration of cyclic polydiorganosiloxanes, are well known in the art.

Ingredient b)

The SiH terminated organopolysiloxanes useful in the process of the present invention can be represented by the formula M'DM', where "M'" means a siloxane unit of formula $R^7_2HSiO_{1/2}$, "D" means a siloxane unit of formula $R^7_2SiO_{2/2}$, where each $R^7$ is independently a monovalent hydrocarbon group containing 1 to 30 carbon atoms or a monovalent halogenated hydrocarbon group containing 1 to 30 carbon atoms. Ingredient b) may comprise a polyorganohydrogensiloxane of formula: $R^7_2HSiO(R^7_2SiO)_bSiR^7_2H$, where $R^7$ is as defined above, and subscript b is ≥0. Alternatively, subscript b has an average value of at least 2. Alternatively, subscript b may be 2 to 1,000.

SiH terminated organopolysiloxanes for ingredient b) are exemplified by:
vii) dimethylhydrogensiloxy-terminated polydimethylsiloxane,
viii) dimethylhydrogensiloxy-terminated poly(dimethylsiloxane/methylphenylsiloxane)
ix) methyl,phenyl,hydrogensiloxy-terminated polydimethylsiloxane, and
x) a combination of two or more thereof.

Alternatively, the SiH terminated organopolysiloxane is a dimethylhydrogensiloxy-terminated polydimethylsiloxane having the average formula $Me_2HSiO(Me_2SiO)_xSiHMe_2$, where Me represents a methyl group and x is ≥1, alternatively x may be 2 to 100, or alternatively x may be 2 to 50. SiH terminated organopolysiloxanes and methods for their preparation, such as hydrolysis and condensation of organohalosilanes, are known in the art.

Ingredient c)

Hydrosilylation involves the reaction between groups and aliphatically unsaturated groups. Suitable hydrosilylation reaction catalysts are known in the art and are commercially available. Such hydrosilylation catalysts can be a metal selected from platinum, rhodium, ruthenium, palladium, osmium, and iridium. Alternatively, the hydrosilylation catalyst may be a compound of such a metal, for example, chloroplatinic acid, chloroplatinic acid hexahydrate, platinum dichloride, and complexes of said compounds with low molecular weight organopolysiloxanes or platinum compounds microencapsulated in a matrix or core/shell type structure. Complexes of platinum with low molecular weight organopolysiloxanes include 1,3-diethenyl-1,1,3,3-tetramethyldisiloxane complexes with platinum. These complexes may be microencapsulated in a resin matrix. Exemplary hydrosilylation catalysts are described in U.S. Pat. Nos. 3,159,601; 3,220,972; 3,296,291; 3,419,593; 3,516,946; 3,814,730; 3,989,668; 4,784,879; 5,036,117; and 5,175,325 and EP 0 347 895 B. Microencapsulated hydrosilylation catalysts and methods of preparing them are known in the art, as exemplified in U.S. Pat. Nos. 4,766,176 and 5,017,654.

The hydrosilylation catalyst can be used in a catalytically effective amount i.e., sufficient to react ingredients a) and b). Alternatively, the catalyst may be used in an amount sufficient to provide 5 ppm to 20 ppm of platinum group metal per total amount of all ingredients used in step I).

d) The Optional Solvent

The hydrosilylation reaction can be conducted neat or in the presence of ingredient d), a solvent. The solvent can be an alcohol such as methanol, ethanol, propanol (including n-propanol and isopropanol), butanol (and branched and linear isomers thereof, a ketone such as acetone, methylethyl ketone, or methyl isobutyl ketone; an aromatic hydrocarbon such as benzene, toluene, or xylene; an aliphatic hydrocarbon such as heptane, hexane, or octane; a glycol ether such as propylene glycol methyl ether, dipropylene glycol methyl ether, propylene glycol n-butyl ether, propylene glycol n-propyl ether, or ethylene glycol n-butyl ether, a halogenated hydrocarbon such as dichloromethane, 1,1,1-trichloroethane or methylene chloride, chloroform, dimethyl sulfoxide, dimethyl formamide, acetonitrile, tetrahydrofuran, white spirits, mineral spirits, or naphtha.

The amount of solvent can be up to 70 weight percent, alternatively 20 to 50 weight percent, said weight percent being based on the total weight of ingredients used in step I). The solvent used during the hydrosilylation reaction can be subsequently removed from the resulting silicone block copolymer having aminofunctional endblocking groups by various known methods.

Step I) effects a hydrosilylation reaction, wherein the SiH units react with the aliphatically unsaturated organic group of ingredient a) to form an Si—C bond. The reaction may be conducted under those conditions known in the art for effecting hydrosilylation reactions.

Additional components can be added to the hydrosilylation reaction which are known to enhance such reactions. These components include salts such as sodium acetate which have a buffering effect in combination with platinum catalysts.

The amount of ingredients a) and b) used in the method described herein may vary, provided the SiH/Vi ratio is >1, alternatively SiH/Vi ratio may range from 1.05 to 2, alternatively from 1.2 to 2. Although, not wishing to be bound by any theory, the present inventors believe reacting ingredients a), b), and c) in step I) provides a reaction product comprising a silicone block copolymer having terminal SiH units, which has formula e)

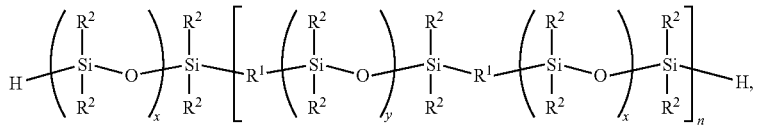

where $R^1$ and $R^2$, and subscripts x, y, and n are as described above. These terminal silicon bonded hydrogen atoms in this formula may be further reacted in step II), for example, when step II) is performed during and/or after step I). Alternatively, step II) may be performed before and/or during step I). The epoxide having at least one aliphatically unsaturated hydrocarbon group may react with the terminal silicon bonded hydrogen on ingredient b) the SiH terminated organopolysiloxane described above, on ingredient e) the silicone block copolymer having terminal SiH units in the silicone block copolymer shown above, or both. Without wishing to be bound by theory, it is thought that when the epoxide having at least one aliphatically unsaturated hydrocarbon group reacts with the terminal silicon bonded hydrogen on ingredient b), an organopolysiloxane terminated at one end with an SiH unit and terminated at the other end with an epoxy functional group will form; and the SiH unit on resulting product of this reaction will react with ingredient a) to terminate the silicone block copolymer. Without wishing to be bound by theory, it is thought that when the epoxide having at least one aliphatically unsaturated hydrocarbon group reacts with the terminal SiH units on the silicone block copolymer having terminal SiH units, it is thought that this will form an epoxide terminated silicone block copolymer of formula

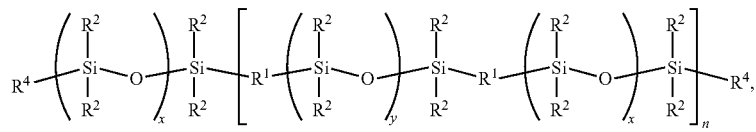

where each $R^4$ is independently an epoxide functional group.

In step II) of the process described above, an epoxide having at least one aliphatically unsaturated group is used. Exemplary epoxides suitable for use in the process may have the formula:

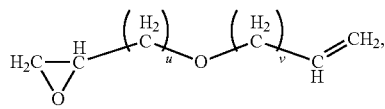

where subscript u is 1 to 10 and subscript v is 1 to 10. Suitable epoxides having at least one aliphatically unsaturated group are commercially available. Representative, non-limiting examples of the epoxide having at least one aliphatically unsaturated group suitable for use in the process include:

allyl glycidyl ether, CAS 106-92-3;
vinylcyclohexene oxide, CAS 106-86-5;
5,6-epoxy-1-hexene, (or 1,2-epoxy-5-hexene and 2-(3-butenyl)oxirane), CAS: 10353-53-4;
9,10-epoxy-1 decene, (or 2-(7-octenyl)oxirane and 1,2-epoxy-9-decene) CAS: 85721-25-1;
7,8-epoxy-1-octene, (or 1,2-epoxy-7-octene and 2-(5-hexenyl) oxirane) CAS: 19600-63-6;
2-vinyloxirane, (or 3,4-epoxy-1-butene, butadiene monoxide) CAS: 930-22-3;
2-methyl-2-vinyloxirane, (or Isoprene monoxide) CAS: 1838-94-4;
Glycidyl acrylate, (or 2-oxiranylniethyl acrylate);
Glycidyl methacrylate, (or 2-oxiranylmethyl 2-methacrylate) CAS: 106-91-2;
Limonene oxide, mixture of cis- and trans-, CAS: 1195-92-2); and
Allyloxy-3,4-epoxytricyclo(5.2.1.0 2,6)decane, CAS: 2279-19-8.

The amount of the epoxide having at least one aliphatically unsaturated group added in step II) may vary, but is typically added in sufficient amount to consume the residual Si—H, that is a molar excess of epoxide to SiH is used. Lower amounts of the epoxide may be used if limiting free epoxide is desired, with the understanding that only partial endblocking will be achieved.

Step I) and step II) may be carried out sequentially or simultaneously. In one embodiment step I) and step II) are conducted sequentially to build molecular weight of the SiH terminated silicone block copolymer before consuming the final quantities of Si—H with an excess of the epoxide endcapping group. Alternatively, step I) and step II) are performed simultaneously or sequentially with step II) before step I) such that the epoxide having at least one aliphatically unsaturated group reacts with terminal SiH units before completing of the molecular weight building in the silicone block copolymer backbone.

Step III) in the process involves reacting the epoxide terminated silicone block copolymer with an amine compound to form the silicone block copolymer having aminofunctional terminal groups. Step III) effects a ring opening reaction of the epoxide by the addition of an amine compound. The product of step III) comprises the silicone block copolymer having an aminofunctional endblocking group as described above.

The amine compound used in step III) may be a primary or secondary amine. Representative, non limiting examples include: $(CH_3)NH_2$, $(CH_3)_2NH$, $(CH_3CH_2)NH_2$, $(CH_3CH_2)_2NH$, $(CH_3CH_2)_3N$, $(HOCH_2CH_2)_2NH$, and $(CH_3CH(OH)CH_2)_2NH$, and bis(2-hydroxypropyl)amine (DIPA). Alternatively, the amine compound may include cyclic amines. Representative non-limiting examples of suitable cyclic amines include:

1-(2-hydroxyethyl)piperazine,
Piperazine,
Pyrrolidine, CAS: 123-75-1
Piperidine, CAS: 110-89-4
Morpholine, CAS: 110-91-8
3-Pyrrolidinol, CAS: 40499-83-0
2,5-dimethylpyrrolidine, CAS: 3378-71-0
1-methylpiperazine, CAS: 109-01-3
4-hydroxypiperidine, CAS: 5382-16-1
2,6-dimethylpiperidine, CAS: 504-03-0
1-ethylpiperazine, CAS: 5308-25-8
1-amine-4-methylpiperazine, CAS: 6928-85-4

Isoindoline, CAS: 496-12-8. Alternatively, the amine compound may be an alkanol amine such as bis(2-hydroxypropyl)amine (DIPA).

Alternatively, the silicone block copolymer having aminofunctional endblocking groups described above may be prepared by a process comprising:

I) reacting ingredients comprising
a) a polyorganosiloxane having an aliphatically unsaturated hydrocarbon group at each molecular terminal, and
b) a SiH terminated organopolysiloxane,
c) a hydrosilylation catalyst,
where the molar ratio of amount of ingredient b)/amount of ingredient a) is greater than one, thereby preparing e) an SiH terminated silicone block copolymer of formula

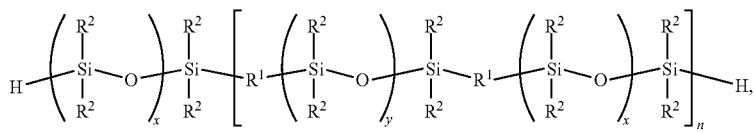

where $R^1$ and $R^2$ and subscripts x, y, and n are as described above;

2) reacting ingredients comprising:
   e) the SiH terminated silicone block copolymer or with ingredient b) the SiH terminated organopolysiloxane, or both ingredient b) and ingredient e), and
   an aliphatically unsaturated alkanol functional amine compound.

Step I) and ingredients a), b), and c) in this process are the same as described above.

The reaction in step 2) is another hydrosilylation reaction. The aliphatically unsaturated alkanol amine may be simply added at the end of step I), and the second hydrosilylation reaction allowed to progress under the same conditions. Alternatively, additional amounts of the hydrosilylation catalyst c) may be added.

The aliphatically unsaturated alkanol functional amine compound may have a formula selected from:

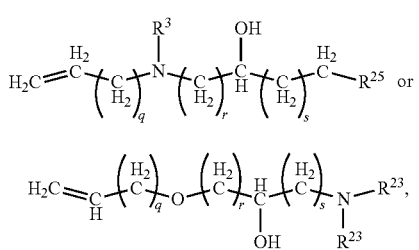

where $R^3$, $R^{25}$, and $R^{23}$ and subscripts q, r, and s are as described above.

The aliphatically unsaturated alkanol functional amine compound of formula (II) used in step 2) may be prepared by a method comprising reacting f) an epoxide having at least one aliphatically unsaturated hydrocarbon group and h) an amine compound. The f) an epoxide having at least one aliphatically unsaturated hydrocarbon group, and h) an amine compound are as described and exemplified above. Alternatively, the aliphatically unsaturated alkanol functional amine compound of formula (I) used in step 2) may be prepared by reacting an aliphatically unsaturated amine and a hydrocarbylene oxide such as an alkylene oxide (e.g., ethylene oxide, propylene oxide (including isopropylene oxide and n-propylene oxide), butylene oxide (including n-butylene oxide, t-butylene oxide, and isobutylene oxide); and pentylene oxide, hexylene oxide, heptylene oxide, octylene oxide, and branched and linear isomers thereof; arylene oxide groups such as phenylene oxide; or an oxiranyl compound such as glycidol.

Step I) and step 2) of this process may be performed simultaneously or sequentially. Alternatively, step I) may be performed before and/or during step 2). Alternatively, step 2) may be performed during or before step 1).

The silicone block copolymer having an aminofunctional endblocking group, described above, may be further reacted to form an amine salt or a quaternary ammonium salt, thereby forming a quat terminal silicone block copolymer. For example, the silicone block copolymer having an aminofunctional endblocking group may be reacted with an alkyl halide or an alkyl sulfate to form a quaternary ammonium salt. The reaction may occur under those conditions known in the art for effecting quaternization of amines. It is not necessary to convert all the amine groups present in the silicone block copolymer having an aminofunctional endblocking group. Thus, those silicone block copolymers having a mixture of amine and quaternary endblocking groups are considered to be within the present invention. Collectively, the silicone block copolymers having an aminofunctional endblocking group, the silicone block copolymers having a quaternary endblocking group, and the silicone block copolymers having both aminofunctional and quaternary endblocking groups are collectively referred to, as "Silicone Block Copolymers").

The Silicone Block Copolymer may be an ingredient in an emulsion composition. As used herein, "emulsion" is meant to encompass water continuous emulsions (for example an oil in water type emulsion, or a silicone in water emulsion), oil or silicone continuous emulsions (water in oil emulsions or water in silicone emulsions), or multiple emulsions (water/oil/water, oil/water/oil types, water/silicone/water, or silicone/water/silicone). The Silicone Block Copolymers may be added to any type of emulsion by common mixing techniques. The addition the Silicone Block Copolymers may occur either during the preparation of the emulsion, or subsequently post added to a pre-formed emulsion. There are no special requirements or conditions needed to effect the mixing of Silicone Block Copolymer of the present disclosure and the emulsion. Mixing techniques can be simple stirring, homogenizing, sonolating, and other mixing techniques known in the art to effect the formation of emulsions. The mixing can be conducted in a batch, semi-continuous, or continuous process.

The amount of Silicone Block Copolymers added to the emulsion can vary and is not limited, however the amounts typically may range from a Silicone Block Copolymer/emulsion weight ratio of 0.1/99 to 99/0.1, alternatively 1/99 to 99/1.

The emulsions used may be w/o, w/s, or multiple phase emulsions using silicone emulsifiers. In one embodiment, the water-in-silicone emulsifier in such formulation is nonionic and is selected from polyoxyalkylene-substituted silicones, silicone alkanolamides, silicone esters and silicone glycosides. Silicone-based surfactants may be used to form such emulsions and are well known in the art, and have been described, for example, in U.S. Pat. No. 4,122,029 to Gee et al., U.S. Pat. No. 5,387,417 to Rentsch, and U.S. Pat. No. 5,811,487 to Schulz et al.

Alternatively, the emulsions containing the Silicone Block Copolymer may contain anionic surfactants, cationic surfactants, amphoteric surfactants, and nonionic surfactants. The anionic surfactants include (i) sulfonic acids and their salt derivatives, including alkyl, aralkyl, alkylnaphthalene, alkyldiphenyl ether sulfonic acids, and their salts, having at least 6 carbon atoms in the alkyl substituent, such as dodecylbenzene sulfonic acid, and its sodium salt or its amine salt; (ii) alkyl sulfates having at least 6 carbon atoms in the alkyl substituent, such as sodium lauryl sulfate; (iii) the sulfate esters of polyoxyethylene monoalkyl ethers; (iv) long chain carboxylic acid surfactants and their salts, such as lauric acid, steric acid, oleic acid, and their alkali metal and amine salts. Some other examples of anionic surfactants are alkali metal sulfosuccinates; sulfonated glyceryl esters of fatty acids such as sulfonated monoglycerides of coconut oil acids; salts of sulfonated monovalent alcohol esters such as sodium oleyl isothionate; amides of amino sulfonic acids such as the sodium salt of oleyl methyl tauride; sulfonated products of fatty acid nitriles such as palmitonitrile sulfonate; sulfonated aromatic hydrocarbons such as sodium alpha-naphthalene monosulfonate; condensation products of naphthalene sulfonic acids with formaldehyde; sodium octahydro anthracene sulfonate; alkali metal alkyl sulfates; ether sulfates having alkyl groups of eight or more carbon atoms such as sodium lauryl ether sulfate; and alkylaryl sulfonates having one or more alkyl groups of eight or more carbon atoms such as neutral salts of hexadecylbenzene sulfonic acid and $C_{20}$ alkylbenzene sulfonic acid.

Commercial anionic surfactants which can be used include the sodium salt of dodecylbenzene sulfonic acid sold under the trademark SIPONATE® DS-10 by Alcolac Inc., Baltimore, Md.; sodium n-hexadecyl diphenyloxide disulfonate sold under the trademark DOWFAX® 8390 by The Dow Chemical Company, Midland, Mich.; the sodium salt of a secondary alkane sulfonate sold under the trademark HOSTAPUR® SAS 60 by Clariant Corporation, Charlotte, N.C.; N-acyl taurates such as sodium N-lauroyl methyl taurate sold under the trademark NIKKOL LMT® by Nikko Chemicals Company, Ltd., Tokyo, Japan; and linear alkyl benzene sulfonic acids sold under the trademark BIO-SOFT® S-100 by the Stepan Company, Northfield, Ill. Compositions of the latter type such as dodecylbenzene sulfonic acid, although a catalyst as noted above, can also function as the anionic surfactant when neutralized. Other suitable surfactants include sodium alkyl sulfonate such as HOSTAPUR® SAS-30. In one embodiment, the emulsifier is triethanolamine dodecylbenzene sulfonate, such as BIO-SOFT® N 300.

Cationic surfactants useful herein include compounds containing quaternary ammonium hydrophilic moieties in the molecule which are positively charged, such as quaternary ammonium salts represented by $R^8R^9R^{10}R^{11}N^+X^-$ where $R^8$ to $R^{11}$ are alkyl groups containing 1-30 carbon atoms, or alkyl groups derived from tallow, coconut oil, or soy; and X is a halogen, e.g., chlorine or bromine. Alternatively, the quaternary ammonium compounds may be alkyl trimethylammonium and dialkyldimethylammonium halides, or acetates, or hydroxides, having at least 8 carbon atoms in each alkyl substituent. Dialkyl dimethyl ammonium salts can be used and are represented by $R^{12}R^{13}N^+(CH_3)_2X^-$ where $R^{12}$ and $R^{13}$ are alkyl groups containing 12-30 carbon atoms or alkyl groups derived from tallow, coconut oil, or soy; and X is halogen. Monoalkyl dimethyl ammonium salts can be used and are represented by $R^{14}N^+(CH_3)_3X^-$ where $R^{14}$ is an alkyl group containing 12-30 carbon atoms or an alkyl group derived from tallow, coconut oil, or soy; and X is halogen, acetate, or hydroxide.

Representative quaternary ammonium halide salts are dodecyltrimethyl ammonium chloride/lauryltrimethyl ammonium chloride (LTAC), cetyltrimethyl ammonium chloride (CTAC), didodecyldimethyl ammonium bromide, dihexadecyldimethyl ammonium chloride, dihexadecyldimethyl ammonium bromide, dioctadecyldimethyl ammonium chloride, dieicosyldimethyl ammonium chloride, didocosyldimethyl ammonium chloride, dicoconutdimethyl ammonium chloride, ditallowdimethyl ammonium chloride, and ditallowdimethyl ammonium bromide. These quaternary ammonium salts are commercially available under trademarks such as ADOGEN®, ARQUAD®, TOMAH®, and VARIQUAT®.

Other suitable cationic surfactants which can be used include (i) fatty acid amines and amides and their salts and derivatives, such as aliphatic fatty amines and their derivatives. Such cationic surfactants that are commercially available include compositions sold under the names Arquad T27 W, Arquad 16-29, by Akzo Nobel Chemicals Inc., Chicago, Ill.; and Ammonyx Cetac-30 by the Stepan Company, Northfield, Ill.

Suitable amphoteric surfactants include; betaines such as cocamidopropylbetaine, sultaines such as cocamidopropylhydroxysultaine, lecithin and hydrogenated lecithin. In one embodiment, the emulsifier is a combination of an anionic and nonionic surfactant. In a further embodiment, the anionic surfactant in the combination is an alkyl sulfonate or a dodecylbenzene sulfonate. In a further embodiment, the nonionic emulsifier is an alkyl-oxo alcohol polyglycol ether or an alkyl polyethylene glycol ether.

Some suitable nonionic surfactants which can be used include polyoxyethylene alkyl ethers, polyoxyethylene alkyl phenyl ethers, alkylglucosides, polyoxyethylene fatty acid esters, sorbitan fatty acid esters, and polyoxyethylene sorbitan fatty acid esters. Nonionic surfactants which are commercially available include compositions such as (i) 2,6,8-trimethyl-4-nonyl polyoxyethylene ether sold under the names Tergitol TMN-6 and Tergitol TMN-10; (ii) the C11-15 secondary alkyl polyoxyethylene ethers sold under the names Tergitol 15-S-7, Tergitol 15-S-9, Tergitol 15-S-15, Tergitol 15-S-30, and Tergitol 15-S-40, by the Dow Chemical Company, Midland, Mich.; octylphenyl polyoxyethylene (40) ether sold under the name Triton X405 by the Dow Chemical Company, Midland, Mich.; (iii) nonylphenyl polyoxyethylene (10) ether sold under the name Makon 10 by the Stepan Company, Northfield, Ill.; (iv) ethoxylated alcohols sold under the name Trycol 5953 by Henkel Corp./Emery Group, Cincinnati, Ohio; (v) ethoxylated alcohols sold under the name Brij L23 and Brij L4 by Croda Inc. Edison, N.J., (vi) alkyl-oxo alcohol polyglycol ethers such as ®GENAPOL UD 050, and Genapol UD110, (vii) alkyl polyethylene glycol ether based on C10-Guerbet alcohol and ethylene oxide such as LUTENSOL® XP 79.

Suitable nonionic surfactants also include poly(oxyethylene)-poly(oxypropylene)-poly(oxyethylene) tri-block copolymers. Poly(oxyethylene)-poly(oxypropylene)-poly(oxyethylene) tri-block copolymers are also commonly known as Poloxamers. They are nonionic triblock copolymers composed of a central hydrophobic chain of polyoxypropylene (poly(propylene oxide)) flanked by two hydrophilic chains of polyoxyethylene (poly(ethylene oxide)). Poly(oxyethylene)-poly(oxypropylene)-poly(oxyethylene) tri-block copolymers are commercially available from BASF (Florham Park, N.J.) and are sold under the tradename PLURONIC®, such as Pluronic L61, L62, L64, L81, P84.

The nonionic surfactant may also be a silicone polyether (SPE), providing the SPE selected as an emulsifier does not have a structure as described above for the polydialkylsiloxane-polyoxyalkylene copolymer as component A). The silicone polyether as an emulsifier may have a rake type structure wherein the polyoxyethylene or polyoxyethylene-polyoxypropylene copolymeric units are grafted onto the siloxane backbone, or the SPE can have an ABA block copolymeric structure wherein A represents the polyether portion and B the siloxane portion of an ABA structure. Suitable silicone polyethers include Dow Corning® 5329 from Dow Corning Corporation of Midland, Mich. USA.

When the emulsion is an oil-in-water emulsion, it may include common ingredients generally used for preparing emulsions such as but not limited to nonionic surfactants well known in the art to prepare o/w emulsions. Examples of nonionic surfactants include polyoxyethylene alkyl ethers, polyoxyethylene alkylphenol ethers, polyoxyethylene lauryl ethers, polyoxyethylene sorbitan monoleates, polyoxyethylene alkyl esters, polyoxyethylene sorbitan alkyl esters, polyethylene glycol, polypropylene glycol, diethylene glycol, ethoxylated trimethylnonanols, and polyoxyalkylene glycol modified polysiloxane surfactants. Commercially available nonionic surfactants which can be used include compositions such as 2,6,8-trimethyl-4-nonyloxy polyethylene oxyethanols (6EO) and (10EO) sold under the trademarks TERGITOL® TMN-6 and TERGITOL® TMN-10; alkyleneoxy polyethylene oxyethanol ($C_{11-15}$ secondary alcohol ethoxylates 7EO, 9EO, and 15EO) sold under the trademarks TERGITOL® 15-S-7, TERGITOL® 15-S-9, TERGITOL® 15-S-15; other $C_{11-15}$ secondary alcohol ethoxylates sold under the trademarks TERGITOL® 15-S-12, 15-S-20, 15-S-30, 15-S-40; and Octylphenoxy polyethoxy ethanol (40EO) sold under the trademark TRITON® X-405. All of these surfactants are sold by Union Carbide Corporation, Danbury, Conn.

Other useful commercial nonionic surfactants are nonylphenoxy polyethoxy ethanol (10EO) sold under the trademark MAKON® 10 by Stepan Company, Northfield, Ill.; polyoxyethylene 23 lauryl ether (Laureth-23) sold commercially under the trademark BRIJ® 35L by ICI Surfactants, Wilmington, Del.; and RENEX® 30, a polyoxyethylene ether alcohol sold by ICI Surfactants, Wilmington, Del.

Protective colloids, i.e., colloidal stabilizers, may be used, if desired, to enhance stability or to provide a specific rheological characteristic to the emulsion. As used herein, the terms "protective colloid" and/or "colloidal stabilizer" mean a nonionic molecule that is an effective agent for protecting charged colloidal particles in an aqueous media against flocculation. These compositions typically have a weight average molecular weight ranging from 1,000-300,000 and are typically more hydrophilic than the composition of the first emulsion polymer, as measured by weight-averaged solubility parameters. Colloidal stabilizers which can be used include hydroxyethyl cellulose having a weight average molecular weight between 50,000-150,000; N-vinyl pyrrolidone; polyvinyl alcohol having a weight average molecular weight between 10,000-200,000; partially acetylated polyvinyl alcohol; carboxymethyl cellulose; gums such as gum arabic; starches; proteins; and mixtures thereof. Preferred colloidal stabilizers are hydroxethyl cellulose and polyvinyl alcohol.

Since emulsions are susceptible to microbiological contamination a preservative can be added. Representative preservatives, which can be used include phenoxyethanol and ethylhexylglycerin; formaldehyde; 1,3-dimethylol-5,5-dimethyl hydantoin, e.g., DMDM Hydantoin; 5-bromo-5-nitro-1,3-dioxane; methyl or propyl paraben; sorbic acid; imidazolidinyl urea; and KATHON® CG (5-chloro-2-methyl-4-isothiazolin-3-one); caprylyl glycol; phenoxyethanol; benzyl alcohol; and/or benzoic acid.

Generally, the silicone emulsions contain a Silicone Block Copolymer concentration of 10 to 70 percent by weight based on the weight of the total emulsion, alternatively 20 to 60 percent by weight. While emulsions containing less than 10 percent Silicone Block Copolymer content can be made, such emulsions may have little or no economic value. The surfactant is generally present at 0.05% to 30% based on the weight of the total emulsion, alternatively 0.1% to 20%. Water and optional ingredients constitute the balance of the emulsion to 100%.

This invention further relates to a treatment method comprising applying to a substrate (e.g., a textile or other fiber) the Silicone Block Copolymer or emulsion thereof, either of which are also referred herein as the treatment composition. The amount applied is a "hand improving" effective amount of the treatment composition and is applied to the fiber and/or textile and/or other substrate by any convenient method. The term "Hand" as used herein means the softness and smoothness of the substrate, e.g., fabric. For example, the treatment composition can be applied by padding, dipping, spraying or exhausting. When the treatment composition comprises more than one solution, dispersion, or emulsion; the solutions, dispersions, and emulsions can be applied simultaneously or sequentially to the substrates, e.g., textiles. After the treatment composition is applied to the substrate, e.g., fiber and/or fabric, it can be dried under ambient conditions or by heating.

The treatment composition can be applied to the substrate, e.g., fiber and/or textile during making the fibers or textiles, or later such as during laundering textiles. After application, carriers (if any) can be removed from the treatment composition for example by drying the composition at ambient or elevated temperature. The amount of treatment composition applied to the substrate, e.g., fibers and textiles is typically sufficient to provide 0.1 to 15 weight percent of the composition on the substrate, based on the dry weight of the substrate, alternatively in an amount of 0.2 to 5 weight percent based on the dry weight of the substrate.

Fibers and textiles that can be treated with the treatment composition include natural fibers such as cotton, silk, linen, and wool; regenerated fibers such as rayon and acetate; synthetic fibers such as polyesters, polyamides, polyacrylonitriles, polyethylenes, and polypropylenes; combinations, and blends thereof. The form of the fibers can include threads, filaments, tows, yarns, woven fabrics, knitted materials, non-woven materials, paper, and carpet. For purposes of this application, additional substrates can be treated with the treatment composition, including leather. Without wishing to be bound by theory, it is thought that textiles treated with the silicone block copolymer have a feel or hand comparable to conventional hydrophobic silicone, but do not significantly impact negatively on the hydrophilicity of the textile.

The Silicone Block Copolymer described above and/or emulsions containing the Silicone Block Copolymer, may alternatively be formulated into personal care products. The personal care products of this invention may be in the form of a cream, a gel, a powder, a paste, or a freely pourable liquid. Generally, such products can generally be prepared at room temperature if no solid materials at room temperature are presents in the compositions, using simple propeller mixers, Brookfield counter-rotating mixers, or homogenizing mixers. No special equipment or processing conditions are typically required. Depending on the type of form made, the method of preparation will be different, but such methods are known in the art.

The personal care products may be functional with respect to the portion of the body to which they are applied, cosmetic, therapeutic, or some combination thereof. Conventional examples of such products include, but are not limited to: antiperspirants and deodorants, skin care creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers, hair shampoos, hair conditioners (either leave in or rinse off), hair colorants, hair relaxants, hair styling aids such as sprays, fixatives, mousses, and/or gels; permanents, depilatories, and cuticle coats, make-ups, color cosmetics, foundations, concealers, blushes, lipsticks, eyeliners, mascara, oil removers, color cosmetic removers, and powders, medicament creams, pastes or sprays including antiacne, dental hygienic, antibiotic, healing promotive, and/or nutritive, which may be preventative and/or therapeutic. In general the personal care products may be formulated with a carrier that permits application in any conventional form, including but not limited to liquids, rinses, lotions, creams, pastes, gels, foams, mousses, ointments, sprays, aerosols, soaps, sticks, soft solids, solid gels, and gels. What constitutes a suitable carrier would be apparent to one of ordinary skill in the art.

The Silicone Block Copolymer described above and/or emulsions containing the Silicone Block Copolymer can be used in a variety of personal, household, and healthcare applications. In particular, the Silicone Block Copolymer and/or emulsions containing the Silicone Block Copolymer may be used in the personal care products disclosed in U.S. Pat. No. 6,051,216 to Barr et al.; U.S. Pat. No. 5,919,441 to Mendolia et al.; U.S. Pat. No. 5,981,680 to Petroff et al.; as disclosed in U.S. Patent Application 2010/0098648 to Yu. and WO 2004/060101 to Yu; in sunscreen compositions as disclosed in U.S. Pat. No. 6,916,464 to Hansenne et al.; in cosmetic compositions also containing film-forming resins, as disclosed in WO2003/105801 to Yu; in the cosmetic compositions as disclosed in U.S. Patent Application 2003/0235553 to Lu, U.S. Patent Application 2003/0072730 to Tornilhac, U.S. Patent Application 2003/0170188 to Ferrari et al., EP 1,266,647 to Tornilhac, EP 1,266,648 to Ferrari, et al., EP1,266,653 to Ferrari et al., WO2003/105789 to Lu, WO2004/000247 to Lu and WO2003/106614 to Lu; as additional agents to those disclosed in WO2004/054523 to Tournilhac; in long wearing cosmetic compositions as disclosed in US Patent Application Publication 2004/0180032; in transparent or translucent care and/or make up compositions as discussed in WO 2004/054524; all of which are incorporated herein by reference.

The personal care products according to this invention can be used by the standard methods, such as applying them to the human body, e.g., skin or hair, using applicators, brushes, applying by hand, pouring them and/or possibly rubbing or massaging the composition onto or into the body. Removal methods, for example for color cosmetics are also well known standard methods, including washing, wiping, peeling and the like. For use on the skin, the personal care products according to the present invention may be used in a conventional manner for example for conditioning the skin. An effective amount of the composition for the purpose is applied to the skin. Such effective amounts generally range from 1 mg/cm$^2$ to 3 mg/cm$^2$. Application to the skin typically includes working the composition into the skin. This method for applying to the skin comprises the steps of contacting the skin with the composition in an effective amount and then rubbing the composition into the skin. These steps can be repeated as many times as desired to achieve the desired benefit.

The use of the personal care products according to the invention on hair may use a conventional manner for conditioning hair. An effective amount of the composition for conditioning hair is applied to the hair. Such effective amounts generally range from 0.5 g to 50 g, alternatively from 1 g to 20 g. Application to the hair typically includes working the composition through the hair such that most or all of the hair is contacted with the product. This method for conditioning the hair comprises the steps of applying an effective amount of the hair care product to the hair, and then working the composition through the hair. These steps can be repeated as many times as desired to achieve the desired conditioning benefit.

Non-limiting examples of additives which may be formulated into the personal care products in addition to the Silicone Block Copolymer described above and/or emulsions containing the Silicone Block Copolymer, include: additional silicones, anti-oxidants, cleansing agents, colorants, additional conditioning agents, deposition agents, electrolytes, emollients and oils, exfoliating agents, foam boosters, fragrances, humectants, occlusive agents, pediculicides, pH control agents, pigments, preservatives, biocides, other solvents, stabilizers, sun-screening agents, suspending agents, tanning agents, other surfactants, thickeners, vitamins, botanicals, fragrances, waxes, rheology-modifying agents, anti-dandruff, anti-acne, anti-carie and wound healing-promotion agents.

The personal care product, such as a shampoo or cleanser may contain at least one anionic detersive surfactant. This can be any of the well-known anionic detersive surfactants typically used in shampoo formulations. These anionic detersive surfactants function as cleansing agents and foaming agents in the shampoo compositions of this invention. The anionic detersive surfactants are exemplified by alkali metal sulforicinates, sulfonated glyceryl esters of fatty acids such as sulfonated monoglycerides of coconut oil acids, salts of sulfonated monovalent alcohol esters such as sodium oleylisethianate, amides of amino sulfonic acids such as the sodium salt of oleyl methyl tauride, sulfonated products of fatty acids nitriles such as palmitonitrile sulfonate, sulfonated aromatic hydrocarbons such as sodium alpha-naphthalene monosulfonate, condensation products of naphthalene sulfonic acids with formaldehyde, sodium octahydroanthracene sulfonate, alkali metal alkyl sulfates such as sodium lauryl sulfate, ammonium lauryl sulfate or triethanol amine lauryl sulfate, ether sulfates having alkyl groups of 8 or more carbon atoms such as sodium lauryl ether sulfate, ammonium lauryl ether sulfate, sodium alkyl aryl ether sulfates, and ammonium alkyl aryl ether sulfates, alkylarylsulfonates having 1 or more alkyl groups of 8 or more carbon atoms, alkylbenzenesulfonic acid alkali metal salts exemplified by hexylbenzenesulfonic acid sodium salt, octylbenzenesulfonic acid sodium salt, decylbenzenesulfonic acid sodium salt, dodecylbenzenesulfonic acid sodium salt, cetylbenzenesulfonic acid sodium salt, and myristylbenzenesulfonic acid sodium salt, sulfuric esters of polyoxyethylene alkyl ether including $CH_3(CH_2)_6CH_2O(C_2H_4O)_2SO_3H$, $CH_3(CH_2)_7CH_2O(C_2H_4O)_{3.5}SO_3H$, $CH_3(CH_2)_8CH_2O(C_2H_4O)_8SO_3H$, $CH_3(CH_2)_{19}CH_2O(C_2H_4O)_4SO_3H$, and $CH_3(CH_2)_{10}CH_2O(C_2H_4O)_6SO_3H$, sodium salts, potassium salts, and amine salts of alkylnaphthylsulfonic acid. Alternatively, the detersive surfactant is selected from the group consisting of sodium lauryl sulfate, ammonium lauryl sulfate, triethanolamine lauryl sulfate, sodium lauryl ether sulfate, and ammonium lauryl ether sulfate. The anionic detersive surfactant is present in the shampoo compositions of this invention in an amount from 5% to 50% and alternatively 5% to 25% based on the total weight of the personal care product.

The personal care product may contain at least one cationic deposition aid, alternatively a cationic deposition polymer. The cationic deposition aid may be present in amounts ranging from 0.001% to 5%, alternatively 0.01% to 1%, and alternatively 0.02% to 0.5% based on total weight of all ingredients in the personal care product. The cationic deposition polymer may be a homopolymer or be formed from two or more types of monomers. The molecular weight of the cationic deposition polymer may be at least 10,000, alternatively may range from 5,000 to 10,000,000, alternatively, and alternatively 100,000 to 2,000,000. The cationic deposition polymers will have cationic nitrogen containing groups such as quaternary ammonium or protonated amino groups, or a mixture thereof. The cationic charge density may be at least 0.1 meq/g, alternatively above 0.8 or higher. The cationic charge density should not exceed 4 meq/g, it is alternatively less than 3; and alternatively less than 2 meq/g. The charge density can be measured using the Kjeldahl method and should be within the above limits at the desired pH of use, which may range from 3 to 9; alternatively 4 to 8. The cationic nitrogen-containing group will generally be present as a substituent on a fraction of the total monomer units of the cationic deposition polymer. Thus when the cationic deposition polymer is not a homopolymer it can contain spacer noncationic monomer units. Such polymers are described in the CTFA Cosmetic Ingredient Directory, 3rd edition. Suitable cationic deposition aids include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers may have alkyl groups of 1 to 7 carbon atoms, alternatively alkyl groups of 1 to 3 carbon atoms. Other suitable spacers include vinyl esters, vinyl alcohol, maleic anhydride, propylene glycol and ethylene glycol. The cationic amines can be primary, secondary or tertiary amines, depending upon the particular species and the pH of the composition. In general secondary and tertiary amines, alternatively tertiary may be used. Amine substituted vinyl monomers and amines can be polymerized in the amine form and then converted to ammonium by quaternization. Suitable cationic amino and quaternary ammonium monomers include, for example, vinyl compounds substituted with dialkyl aminoalkyl acrylate, dialkylamino alkylniethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, and quaternized pyrrolidine, e.g., alkyl vinyl imidazolium, alkyl vinyl pyridinium, alkyl vinyl pyrrolidine salts. The alkyl portions of these monomers may be lower alkyls such as the alkyl groups of 1 to 4 carbon atoms, alternatively alkyl groups of 1 to 2 carbon atoms. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide. The cationic deposition aids can comprise mixtures of monomer units derived from amine- and/or quaternary ammonium-substituted monomer and/or compatible spacer monomers. Suitable cationic deposition aids include, for example: copolymers of 1-vinyl-2-pyrrolidine and 1-vinyl-3-methylimidazolium salt (e.g., Chloride salt) (referred to in the industry by the Cosmetic, Toiletry, and Fragrance Association, "CTFA". as Polyquaternium-16) such as those commercially available from BASF Wyandotte Corp. (Parsippany, N.J., USA) under the LUVIQUAT tradename (e.g., LUVIQUAT FC 370); copolymers of 1-vinyl-2-pyrrolidine and dimethylaminoethyl methacrylate (referred to in the industry by CTFA as Polyquaternium-11) such as those commercially from Gar Corporation (Wayne, N.J., USA) under the GAFQUAT tradename (e.g., GAFQUAT 755N); cationic diallyl quaternary ammonium-containing polymer including, for example, dimethyldiallyammonium chloride homopolymer and copolymers of acrylamide and dimethyldiallyammonium chloride, referred to in the industry (CTFA) as Polyquatemium 6 and Polyquaternium 7, respectively; mineral acid salts of aminoalkyl esters of homo- and co-polymers of unsaturated carboxylic acids having from 3 to 5 carbon atoms, as described in U.S. Pat. No. 4,009,256 to Nowak Jr., et al.; and cationic polyacrylamides as described in U.S. Pat. No. 5,543,074 to Hague et al. Other cationic deposition aids that can be used include polysaccharide polymers, such as cationic cellulose derivatives and cationic starch derivatives. Cationic polysaccharide polymer materials suitable for use in compositions of the invention include those of the formula: —O($R^{15}$—N+$R^{16}R^{17}R^{18}$X—) wherein: A is an anhydroglucose residual group, such as starch or cellulose anhydroglucose residual, $R^{15}$ is an alkylene oxyalklene, polyoxyalkylene, or hydroxyalkylene group, or combination thereof, $R^{16}$, $R^{17}$ and $R^{18}$ independently are alkyl, aryl, alkylaryl, arylalkyl, alkoxyalkyl, or alkoxyaryl groups, each group containing up to 18 carbon atoms, and the total number of carbon atoms for each cationic moiety (i.e., the sum of carbon atoms in $R^{16}$, $R^{17}$ and $R^{18}$) may 20 or less, and X is an anionic counterion, as previously described. Cationic cellulose is available from Amerchol Corp. (Edison, N.J., USA) in their Polymer iR (trade mark) and LR (trade mark) series of polymers, as salts of hydroxyethyl cellulose reacted with trimethyl ammonium substituted epoxide, referred to in the industry (CTFA) as Polyquatemium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200. Other cationic deposition aids that can be used include cationic guar gum derivatives, such as guar hydroxypropyltrimonium chloride (Commercially available from Celanese Corp. in their Jaguar trademark series). Other materials include quaternary nitrogen-containing cellulose ethers (e.g., as described in U.S. Pat. No. 3,962,418 to Birkofer, incorporated by reference herein), and copolymers of etherified cellulose and starch (e.g., as described in U.S. Pat. No. 3,958,581 to Abegg et al., incorporated by reference herein).

The personal care product may contain a foam boosting agent. A foam booster is an agent which increases the amount of foam available from a system at a constant molar concentration of surfactant, in contrast to a foam stabilizer which delays the collapse of a foam. Foam building is provided by adding to the aqueous media an effective amount of a foam boosting agent. The foam boosting agent may be selected from the group consisting of fatty acid alkanolamides and amine oxides. The fatty acid alkanolamides are exemplified by isostearic acid diethanolamide, lauric acid diethanolamide, capric acid diethanolamide, coconut fatty acid diethanolamide, linoleic acid diethanolamide, myristic acid diethanolamide, oleic acid diethanolamide, stearic acid diethanolamide, coconut fatty acid monoethanolamide, oleic acid monoisopropanolamide, and lauric acid monoisopropanolamide. The amine oxides are exemplified by N-cocodimethylamine oxide, N-lauryl dimethylamine oxide, N-myristyl dimethylamine oxide, N-stearyl dimethylamine oxide, N-cocamidopropyl dimethylamine oxide, N-tallowamidopropyl dimethylamine oxide, bis(2-hydroxyethyl) C12-15 alkoxypropylamine oxide. Alternatively, a foam booster may be selected from the group consisting of lauric acid diethanolamide, N-lauryl dimethylamine oxide, coconut acid diethanolamide, myristic acid diethanolamide, and oleic acid diethanolamide. The foam boosting agent may be present in the shampoo compositions of this invention in an amount of 1% to 15%, alternatively 2% to 10% based on the total weight of the shampoo composition. The shampoo composition may further comprise a polyalkylene glycol to improve lather performance. Concentration of the polyalkylene glycol in the shampoo composition may range from 0.01% to 5%, alternatively from 0.05% to 3%, and alternatively 0.1% to 2%, by weight of the composition. The optional polyalkylene glycols are characterized by the general formula: $H(OCH_2CHR^{19})_t$—OH where $R^{19}$ is selected from the group consisting of H, methyl, and mixtures thereof. When $R^{19}$ is H, these materials are polymers of ethylene oxide, which are also known as polyethylene oxides, polyoxyethylenes, and polyethylene glycols. When $R^{19}$ is methyl, these materials are polymers of propylene oxide, which are also known as polypropylene oxides, polyoxypropylenes, and polypropylene glycols. When $R^{19}$ is methyl, it is also understood that various positional isomers of the resulting polymers can exist. In the above structure, subscript t has an average value of 1,500 to 25,000, alternatively 2,500 to 20,000, and alternatively 3,500 to 15,000. Polyethylene glycol polymers useful herein are PEG-2M wherein $R^{19}$ equals H and subscript t has an average value of 2,000 (PEG-2M is also known as Polyox WSR9 N-10, which is available from Union Carbide and as PEG-2,000); PEG-5M wherein $R^{19}$ equals H and t has an average value of 5,000 (PEG-5M is also known as Polyox WSRO N-35 and Polyox WSRS N-80, both available from Union Carbide and as PEG-5,000 and Polyethylene Glycol 300,000); PEG-7M wherein $R^{19}$ equals H and t has an average value of 7,000 (PEG-7M is also known as Polyox WSRO N-750 available from Union Carbide); PEG-9M where $R^{19}$ equals H and t has an average value of 9,000 (PEG 9-M is also known as Polyox WSRS N-3333 available from Union Carbide); and PEG14 M wherein $R^{19}$ equals H and t has an average value of 14,000 (PEG-14M is also known as Polyox WSRO N-3000 available from Union Carbide). Other useful polymers include the polypropylene glycols and mixed polyethylene/polypropylene glycols.

The personal care product may contain a suspending agent at concentrations effective for suspending the silicone conditioning agent, or other water-insoluble material, in dispersed form in the shampoo compositions. Such concentrations range from 0.1% to 10%, alternatively from 0.3% to 5.0%, by weight of the shampoo compositions. Suspending agents include crystalline suspending agents which can be categorized as acyl derivatives, long chain amine oxides, and mixtures thereof, concentrations of which range from 0.1% to 5.0%, alternatively from 0.5% to 3.0%, by weight of the shampoo compositions. These suspending agents are described in U.S. Pat. No. 4,741,855 to Grote et al., which description is incorporated herein by reference. These suspending agents include ethylene glycol esters of fatty acids alternatively having from 16 to 22 carbon atoms. Alternatively, the suspending agents are the ethylene glycol stearates, both mono and distearate, but particularly the distearate containing less than 7% of the mono stearate. Other suitable suspending agents include alkanol amides of fatty acids, having from 16 to 22 carbon atoms, alternatively 16 to 18 carbon atoms, examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the materials listed above may be used as suspending agents. For example, it is contemplated that suspending agents with long chain hydrocarbyls having 8 to 22 carbon atom chains may be used. Other long chain acyl derivatives suitable for use as suspending agents include N,N-dihydrocarbyl amido benzoic acid and soluble salts thereof (e.g., Na, K), particularly N,N-di(hydrogenated) C16, C18 and tallow amido benzoic acid species of this family, which are commercially available from Stepan Company (Northfield, Ill., USA). Examples of suitable long chain amine oxides for use as suspending agents include alkyl (C16-C22) dimethyl amine oxides, e.g., stearyl dimethyl amine oxide. Other suitable suspending agents include xanthan gum at concentrations ranging from 0.3% to 3%, alternatively 0.4% to 1.2%, by weight of the shampoo compositions. The use of xanthan gum as a suspending agent in silicone containing shampoo compositions is described, for example, in U.S. Pat. No. 4,788,006 to Bolich et al., which description is incorporated herein by reference. Combinations of long chain acyl derivatives and xanthan gum may also be used as a suspending agent in the shampoo compositions. Such combinations are described in U.S. Pat. No. 4,704,272 to Oh et al., which description is incorporated herein by reference. Other suitable suspending agents include carboxyvinyl polymers. Among these polymers are the copolymers of acrylic acid crosslinked with polyallylsucrose as described in U.S. Pat. No. 2,798,053 to Brown, which description is incorporated herein by reference. Examples of these polymers include Carbopol 934, 940, 941, and 956, available from B. F. Goodrich Company. Other suitable suspending agents include primary amines having a fatty alkyl moiety having at least 16 carbon atoms, examples of which include palmitamine or stearamine, and secondary amines having two fatty alkyl moieties each having at least 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer. Other suitable suspending agents may be used in the shampoo compositions, including those that can impart a gel-like viscosity to the composition, such as water soluble or colloidally water soluble polymers like cellulose ethers (e.g., methylcellulose, hydroxybutyl methylcellulose, hyroxypropylcellulose, hydroxypropyl methylcellulose, hydroxyethyl ethylcellulose and hydroxyethylcellulose), guar gum, polyvinyl alcohol, polyvinyl pyrrolidone, hydroxypropyl guar gum, starch and starch derivatives, viscosity modifiers, and gelling agents.

The personal care composition may contain one or more water-soluble emollients including, but not limited to, lower molecular weight aliphatic diols such as propylene glycol and butylene glycol; polyols such as glycerine and sorbitol; and polyoxyethylene polymers such as polyethylene glycol 200. The specific type and amount of water soluble emollient(s) employed will vary depending on the desired aesthetic characteristics of the composition, and is readily determined by one skilled in the art.

The personal care product may contain various oils. The term "oil" as used herein refers to any material which is substantially insoluble in water. When the compositions comprising the Silicone Block Copolymer described above and/or emulsions containing the Silicone Block Copolymer, is to be used in a cosmetic or other personal care product, the product components must also be cosmetically acceptable or otherwise meet the conditions of the end use product. Suitable oil components include, but are not limited to, natural oils such as coconut oil; hydrocarbons such as mineral oil and hydrogenated polyisobutene; fatty alcohols such as octyldodecanol; esters such as C12-C15 alkyl benzoate; diesters such as propylene dipelargonate; and triesters, such as glyceryl trioctanoate and silicones especially cyclomethicone and dimethicone and mixtures thereof. The composition comprising the Silicone Block Copolymer described above and/or emulsions containing the Silicone Block Copolymer, may also contain oils, alternatively a mixture of low viscosity and high viscosity oils. Suitable low viscosity oils have a viscosity of 5 to 100 mPa·s at 25° C., and are generally esters having the structure $R^{20}CO—OR^{21}$ wherein $R^{20}CO$ represents the carboxylic acid radical and wherein $OR^{21}$ is an alcohol residue. Examples of these low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or mixtures of octyldodecanol, acetylated lanolin alcohol, cetyl acetate, isododecanol, polyglyceryl-3-diisostearate, or mixtures thereof. The high viscosity surface oils generally have a viscosity of 200-1,000,000 mPa·s at 25° C., alternatively a viscosity of 100,000-250,000 mPa·s. Surface oils include castor oil, lanolin and lanolin derivatives, triisocetyl citrate, sorbitan sesquioleate, C10-18 triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or mixtures thereof. The suggested ratio of low viscosity to high viscosity oils in the oil phase is 1:15 to 15:1, alternatively 1:10 to 10:1 respectively. Alternatively, the formulation comprises 1 to 20% of a mixture of low viscosity and high viscosity surface oils.

Among the optional other non-silicone fatty substances, of mineral oils, such as liquid paraffin or liquid petroleum, of animal oils, such as perhydrosqualene or arara oil, or alternatively of vegetable oils, such as sweet almond, calophyllum, palm, castor, avocado, jojoba, olive or cereal germ oil may be added to a personal care product containing the Silicone Block Copolymer described above and/or emulsions containing the Silicone Block Copolymer. It is also possible to use esters of lanolic acid, of oleic acid, of lauric acid, of stearic acid or of myristic acid, for example; alcohols, such as oleyl alcohol, linoleyl or linolenyl alcohol, isostearyl alcohol or octyldodecanol; or acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, trior sucroglycerides; lanolins; or fatty esters which are solid at 25° C.

The personal care product may contain various waxes. The waxes or wax-like materials generally have a melting point range of 35 to 120° C. at atmospheric pressure. Waxes in this category include synthetic wax, ceresin, paraffin, ozokerite, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, or mixtures thereof. Mention may be made, among the waxes capable of being used as non-silicone fatty substances, of animal waxes, such as beeswax; vegetable waxes, such as carnauba, candelilla, ouricury or japan wax or cork fibre or sugarcane waxes; mineral waxes, for example paraffin or lignite wax or microcrystalline waxes; synthetic waxes, including polyethylene waxes, and waxes obtained by the Fischer-Tropsch synthesis. Mention may be made, among the silicone waxes, of polymethylsiloxane alkyls, alkoxys and/or esters.

A thickening agent may be added to provide a convenient viscosity. For example, viscosities within the range of 500 to 25,000 mm²/s at 25° C. or alternatively in the range of 3,000 to 7,000 mm²/s are usually suitable. Suitable thickening agents are exemplified by sodium alginate, gum arabic, polyoxyethylene, guar gum, hydroxypropyl guar gum, ethoxylated alcohols, such as laureth-4 or polyethylene glycol 400, cellulose derivatives exemplified by methylcellulose, methylhydroxypropylcellulose, hydroxypropylcellulose, polypropylhydroxyethylcellulose, starch, and starch derivatives exemplified by hydroxyethylamylose and starch amylose, locust bean gum, electrolytes exemplified by sodium chloride and ammonium chloride, and saccharides such as fructose and glucose, and derivatives of saccharides such as PEG-120 methyl glucose diolate or mixtures of 2 or more of these. Alternatively the thickening agent is selected from cellulose derivatives, saccharide derivatives, and electrolytes, or from a combination of two or more of the above thickening agents exemplified by a combination of a cellulose derivative and any electrolyte, and a starch derivative and any electrolyte. The thickening agent, where used is present in the shampoo compositions of this invention in an amount sufficient to provide a viscosity in the final shampoo composition of from 500 to 25,000 mm²/s. Alternatively the thickening agent is present in an amount from 0.05 to 10 wt % and alternatively 0.05 to 5 wt % based on the total weight of the shampoo composition.

Stabilizing agents can be used in the water phase of the personal care product containing the Silicone Block Copolymer described above and/or emulsions containing the Silicone Block Copolymer. Suitable water phase stabilizing agents can include alone or in combination one or more electrolytes, polyols, alcohols such as ethyl alcohol, and hydrocolloids. Typical electrolytes are alkali metal salts and alkaline earth salts, especially the chloride, borate, citrate, and sulfate salts of sodium, potassium, calcium and magnesium, as well as aluminum chlorohydrate, and polyelectrolytes, especially hyaluronic acid and sodium hyaluronate. When the stabilizing agent is, or includes, an electrolyte, it amounts to 0.1 to 5 wt % and more alternatively 0.5 to 3 wt % of the total composition. The hydrocolloids include gums, such as Xanthan gum or Veegum and thickening agents, such as carboxymethyl cellulose. Polyols, such as glycerine, glycols, and sorbitols can also be used. Alternative polyols are propylene glycol, sorbitol and butylene glycol. If a large amount of a polyol is used, one need not add the electrolyte. However, it is typical to use a combination of an electrolyte, a polyol and an hydrocolloid to stabilize the water phase, e.g. magnesium sulfate, butylene glycol and Xanthan gum.

The personal care product can also be under the form of aerosols in combination With propellant gases, such as carbon dioxide, nitrogen, nitrous oxide, volatile hydrocarbons such as butane, isobutane, or propane and chlorinated or fluorinated hydrocarbons such as dichlorodifluoromethane and dichlorotetrafluoroethane or dimethylether.

Silicone compositions other than the compositions containing Silicone Block Copolymer and/or emulsion containing the Silicone Block Copolymer described above, may also be included in the personal care products. For example, such silicones include; silicone fluids, gums, resins, elastomers; silicone surfactants and emulsifiers such as silicone polyethers, organofunctional silicones such as aminofunctional silicones and alkylmethylsiloxanes.

Alkylmethylsiloxanes may be included in the present compositions. These siloxane polymers may have the formula $Me_3SiO[Me_2SiO]_w[MeR^{22}SiO]_zSiMe_3$, in which $R^{22}$ is a hydrocarbon group containing 6-30 carbon atoms, Me represents methyl, subscript w≥0, subscript z≥0, and the DP, i.e., the sum of w and z is 3 to 50. Both the volatile and liquid species of alkymethysiloxanes can be used in the composition.

Silicone gums may be included in the present compositions. Polydiorganosiloxane gums are known in the art and are available commercially. They consist of generally insoluble polydiorganosiloxanes having a viscosity in excess of 1,000,000 centistoke ($mm^2/s$) at 25° C., alternatively greater than 5,000,000 centistoke ($mm^2/s$) at 25° C. These silicone gums may be sold as compositions already dispersed in a suitable solvent to facilitate their handling. Ultra-high viscosity silicones can also be included as optional ingredients. These ultra-high viscosity silicones typically have a kinematic viscosity greater than 5 million centistoke ($mm^2/s$) at 25° C., to 20 million centistoke ($mm^2/s$) at 25° C. Compositions of this type in the form of suspensions may be used, and are described for example in U.S. Pat. No. 6,013,682 to Dalle et al. (Jan. 11, 2000).

Silicone resins may be included in the present personal care products. These resins are generally highly crosslinked polymeric siloxanes. Crosslinking is obtained by incorporating trifunctional and/or tetrafunctional silanes with the monofunctional silane and/or difunctional silane monomers used during manufacture. The degree of crosslinking required to obtain a suitable silicone resin will vary according to the specifics of the silane monomer units incorporated during manufacture of the silicone resin. In general, any silicone having a sufficient level of trifunctional and tetrafunctional siloxane monomer units, and hence possessing sufficient levels of crosslinking to dry down to a rigid or a hard film can be considered to be suitable for use as the silicone resin. Commercially available silicone resins suitable for applications herein are generally supplied in an unhardened form in low viscosity volatile or nonvolatile silicone fluids. The silicone resins should be incorporated into compositions of the invention in their non-hardened forms rather than as hardened resinous structures.

Silicone carbinol fluids may be included in the present compositions. These materials are described in U.S. Patent Application 2004/0223936 to Fecht et al. and can be commonly described as substituted hydrocarbyl functional siloxane fluids or resins.

When selecting ingredients for the treatment composition and/or the personal care product described above, there may be overlap between types of ingredients because certain ingredients described herein may have more than one function. For example, hydroxyethylcellulose may be useful as a colloidal stabilizer and a thickening agent. When adding additional ingredients to the treatment composition and/or the personal care product, the additional ingredients are distinct from one another.

Exemplary hair care products that can be made with the Silicone Block Copolymer described above include a shampoo comprising:
(1) the Silicone Block Copolymer described above, or the emulsion of the Silicone Block Copolymer described above,
(2) water, and
(3) an anionic surfactant and/or an amphoteric surfactant (e.g., sodium laureth sulfate),
optionally (4) a preservative, and
optionally (5) a cationic deposition polymer, and
optionally (6) a thickener (e.g., carbomer).

Alternatively, the hair care product may be a hair conditioner comprising:
(A) the Silicone Block Copolymer described above, or the emulsion of the Silicone Block Copolymer described above,
(B) water,
optionally (C) a thickener (e.g., Hydroxyethyl-cellulose),
(D) a fatty alcohol (e.g., Cetearyl Alcohol),
optionally (E) other emulsifiers (e.g., PEG-100 Stearate & Glyceryl Stearate),
optionally (F) a preservative (e.g.,), and
optionally (G) a cationic deposition polymer.

Alternatively, the emulsion described above may be used as a leave in hair treatment composition. Alternatively, the hair care composition may be an anhydrous leave in hair treatment composition comprising:
(A) the Silicone Block Copolymer described above, and
(B) an organic or silicone carrier.

EXAMPLES

These examples are intended to illustrate the invention to one of ordinary skill in the art and should not be interpreted as limiting the scope of the invention set forth in the claims. All measurements and experiments were conducted at 23° C., unless indicated otherwise.

Reference Example 1: Synthesis of Allyl Aminohydroxyl Via Amination with bis(2-hydroxypropyl)amine In a 3-neck flask equipped with a reflux condenser, nitrogen sweep, stirrer, temperature controller with thermocouple, and heating mantle, preheated bis(2-hydroxypropyl) amine (DIPA) at 50° C. (79.17 g) and isopropanol (37.29 g) were heated to 50 C. Allyl glycidyl ether (70 g) was added dropwise to the reaction, and the amination reaction was allowed to proceed overnight (15 hours) at 70° C. to ensure complete consumption of DIPA. The reaction setup was modified to a simple distillation apparatus. Isopropanol and excess ally glycidyl ether were removed from the product by vacuum stripping at 120° C. and 20 mmHg for 3 hour. The sample was allowed to cool to less than 70° C. prior to breaking the vacuum with nitrogen and then decanting the product into a glass jar once cooled.

Example 2: Hydrosilylation to 400 Degree of Polymerization (DP) DIPA (Diisopropanolamine) Terminated A three-neck round bottom flask equipped with a reflux condenser, nitrogen sweep, stirrer, temperature controller with thermocouple, and heating mantel was loaded with the material made in Reference Example 1 (1.72 wt %) and SiH terminated siloxane (14.24 wt %), with a SiH concentration of 1600 ppm (20 DP) determined via FT-IR. The flask was heated to 70° C., and 1% solution of Karstedt's catalyst in isopropanol (IPA) was added (5 ppm Pt) as a catalyst. The reaction temperature was held at 70° C. for one hour until the [SiH] reached 1000 ppm to 1100 ppm. The allyl terminated siloxane (84.04 wt %; 179 DP) was then added to the reaction with 1% solution of Karstedt's catalyst in IPA (5 ppm Pt). The reaction was held at 70° C. for 2 hours. Reaction completion ([SiH]<10 ppm) was determined using FT-IR analysis. The viscosity of the final product was determined to be 12,557 cP at room temperature using Brookfield DV-III Ultra (CPE-52 spindle).

Example 3: Hydrosilylation to 600 DP DIPA Terminated

A three-neck round bottom flask equipped with a reflux condenser, nitrogen sweep, stirrer, temperature controller with thermocouple, and heating mantel was loaded with the material made in Reference Example 1 (1.17 wt %) and SiH terminated siloxane (12.91 wt %), with a SiH concentration of 1600 ppm (20 DP) determined via FT-IR. The flask was heated to 70 C, and 1% solution of Karstedt's catalyst in IPA was added (5 ppm Pt) as a catalyst. The reaction temperature was held at 70 C for one hour until the [SiH] reached 1000 ppm to 1100 ppm. The allyl terminated siloxane (85.92 wt %; 179 DP) was then added to the reaction with 1% solution of Karstedt's catalyst in IPA (5 ppm Pt). The reaction was held at 70° C. for 2 hours. Reaction completion ([SiH]<10 ppm) was determined using FT-IR analysis. The viscosity of the final product was determined to be 22,765 cP at room temperature using Brookfield DV-III Ultra (CPE-52 spindle).

Example 4: Hydrosilylation to 1,000 DP DIPA Terminated

A three-neck round bottom flask equipped with a reflux condenser, nitrogen sweep, stirrer, temperature controller with thermocouple, and heating mantel was loaded with the material made in Reference Example 1 (0.72 wt %) and SiH terminated siloxane (11.80 wt %), with a SiH concentration of 1600 ppm (20 DP) determined via FT-IR. The flask was heated to 70 C, and 1% solution of Karstedt's catalyst in IPA was added (5 ppm Pt) as a catalyst. The reaction temperature was held at 70 C for one hour until the [SiH] reached approximately 1300 ppm. The allyl terminated siloxane (87.49 wt %; 179 DP) was then added to the reaction with 1% solution of Karstedt's catalyst in IPA (5 ppm Pt). The reaction was held at 70° C. for 2 hours. Reaction completion ([SiH]<10 ppm) was determined using FT-IR analysis. The viscosity of the final product was determined to be 34,000 cP at room temperature using Brookfield Ultra (CPE-52 spindle).

Example 5: Hydrosilylation of 400 DP DIPA and Alkyl Terminated

A three-neck round bottom flask equipped with a reflux condenser, nitrogen sweep, stirrer, temperature controller with thermocouple, and heating mantel was loaded with the material made in Reference Example 1 (0.87 wt %), 1-hexene (0.27 wt %), and SiH terminated siloxane (14.32 wt %), with a SiH concentration of 1600 ppm (20 DP) determined via FT-IR. The flask was heated to 70° C., and 1% solution of Karstedt's catalyst in IPA was added (5 ppm Pt) as a catalyst. The reaction temperature was held at 70° C. for one hour until the [SiH] reached 1000 ppm to 1100 ppm. The allyl terminated siloxane (84.54 wt %; 179 DP) was then added to the reaction with 1% solution of Karstedt's catalyst in IPA (5 ppm Pt). The reaction was held at 70° C. for 2 hours. Reaction completion ([SiH]<10 ppm) was determined using FT-IR analysis. Final sample was diluted in 10 wt % isofol 12.

Example 6: Preparation of Emulsions (Prophetic)

The emulsification procedure, will be performed on a Hauschild Speedmixer. To a plastic cup will be added the silicone block copolymer prepared in Reference Example 1, Brig 35L surfactant, optionally lactic acid, and a first quantity of water. The mixture will be sheared at maximum speed for 20 seconds. An additional quantity of water will be added, and the emulsion will again be mixed on the Speedmixer. The amounts in each emulsion sample to be prepared are shown in Table 1, below.

TABLE 1

| | Emulsions | | | |
|---|---|---|---|---|
| Ingredient | Amount in Sample 6A | Amount in Sample 6B | Amount in Sample 6C | Amount in Sample 6D |
| Silicone Block Copolymer of Reference Example 1 | 10 | 4 | 10 | 4 |
| Brig 35L Surfactant | 0.5 | 4 | 0.6 | 4 |
| Water, First Quantity + Additional Quantity | 3 + 3 | 2 + 8 | 2 + 4 | 2 + 7 |
| Lactic Acid | none | 0.1 | none | 0.06 |

All amounts in Table 1 are parts by weight.

Example 7: Preparation of Hair Conditioner Formulations (Prophetic)

Samples of emulsions as described in Example 6 will be added to rinse-off conditioning formulations using an amount sufficient to provide 2% the silicone block copolymer. The conditioning formulations are shown in Table 2, below. The conditioners of the present invention will be prepared using Emulsions A, B, C and D from Table 1.

TABLE 2

| | Conditioners | | | |
|---|---|---|---|---|
| Ingredient | Weight Percent | Weight Percent | Weight Percent | Weight Percent |
| Deionized Water | q.s. to 100% | q.s. to 100% | q.s. to 100% | q.s. to 100% |
| Hydroxyethyl-cellulose[1] | 1.5 | 1.5 | 1.5 | 1.5 |
| Cetearyl Alcohol[2] | 1.0 | 1.0 | 1.0 | 1.0 |
| PEG-100 Stearate & Glyceryl Stearate[3] | 1.0 | 1.0 | 1.0 | 1.0 |
| Emulsion 6A | 3.3 | — | — | — |
| Emulsion 6B | — | 10.0 | — | — |
| Emulsion 6C | — | — | 3.4 | — |
| Emulsion 6D | — | — | — | 9.6 |
| Phenoxyethanol and Ethylhexylglycerin[4] | 0.5 | 0.5 | 0.5 | 0.5 |

[1]Natrosol® 250 HHR available from Hercules of Wilmington, DE
[2]Crodocol CS-50® available from Croda Inc. of Edison, NJ
[3]Arlacel® 165 available from Uniqema of Wilmington, DE
[4]Euxyl® PE 9010 available from Schülke & Mayr Example 8—Conditioning Shampoo Formulations (Prophetic)

Samples of emulsions described in Example 6 will be added to shampoo formulations in an amount sufficient to provide 2% of the silicone block copolymer. The shampoo formulations are shown in Table 3. The shampoos of the present invention will be prepared using A, B, C and D emulsions from Table 1.

TABLE 3

Conditioning Shampoos

| Ingredient | Weight % | Weight % | Weight % | Weight % |
|---|---|---|---|---|
| Deionized Water | q.s. to 100% | q.s. to 100% | q.s. to 100% | q.s. to 100% |
| Sodium Laureth Sulfate[1] | 30 | 30 | 30 | 30 |
| Cocamide MIPA[2] | 2.0 | 2.0 | 2.0 | 2.0 |
| Cocamidopropyl Betaine[3] | 7.0 | 7.0 | 7.0 | 7.0 |
| Polyquaternium-10[4] | 0.3 | 0.3 | 0.3 | 0.3 |
| PEG-150 Pentaerythrityl Tetrastearate[5] | 1.5 | 1.5 | 1.5 | 1.5 |
| Emulsion 6A | 3.3 | — | — | — |
| Emulsion 6B | — | 10.0 | — | — |
| Emulsion 6C | — | — | 3.4 | — |
| Emulsion 6D | — | — | — | 9.6 |
| Phenoxyethanol (and) Ethylhexylglycerin[6] | 0.5 | 0.5 | 0.5 | 0.5 |

[1]Standapol ES-3® available from Cognis Corp. of Cincinnati, OH
[2]Mackamide CPA available from Rhodia
[3]Monateric CAB-LC® available from Uniquema of New Castle, DE
[4]UCARE Polymer JR-30M available from Dow/Amerchol of Midland, MI
[5]Crothix ® available from Croda Inc. of Edison, NJ
[6]Euxyl® PE 9010 available from Schülke & Mayr Deionized water is added to the mixing vessel. In order to keep the active silicone loading constant throughout testing, it is necessary to adjust the water level added depending on the percent active silicone in the various emulsions used. With moderate agitation, the polyquaternium-10 is dispersed until fully dissolved. This is then heated to 75° C. and the PEG-150 pentaerythrityl tetrastearate is added with continual mixing. Heat is decreased to 40° C. and sodium lauryl ether sulfate, cocamide MIPA, cocamidopropyl betaine are added in that order. When completely incorporated, silicone block copolymer emulsion is added to the base shampoo. The shampoo is mixed for 5-10 minutes and then Phenoxyethanol (and) Ethylhexylglycerin is added. The water loss is compensated for and the formulation is mixed for an additional 5 minutes. The final pH of the shampoo formulations are approximately 5.5-6.0.

Example 9—Leave-On Conditioner Application (Prophetic)

The emulsions described in Example 6 will be further diluted with water to a 2% concentration of silicone block copolymer.

Reference Example 10 Amination of Glycidol with Allyamine

In a 3-neck flask equipped with a reflux condenser, nitrogen sweep, stirrer, temperature controller with thermocouple, and heating mantle, a mixture of glycidol (37.03%) and toluene or isopropanol (50%) was mixed at room temperature. Allyamine (3.24%) was added dropwise to the reaction, and an exotherm was observed. Once the temperature was stable, the addition of allyamine was repeated 3 more times. The amination reaction was allowed to proceed overnight (15 hours) at room temperature (25° C.) to ensure complete consumption of amine. The reaction setup was modified to a simple distillation apparatus. The toluene/isopropanol and excess glycidol were removed from the product by vacuum stripping at 150° C. and 20 mmHg for 3 hours. The sample was allowed to cool to less than 70° C. prior to breaking the vacuum with nitrogen and then decanting the product into a glass jar.

Example 11. Hydrosilylation of 400 DP Terminated

A three-neck round bottom flask equipped with a reflux condenser, nitrogen sweep, stirrer, temperature controller with thermocouple, and heating mantel was loaded with the endblocker prepared in Reference Example 10 (0.66%) and SiH terminated siloxane (14.39%), with a SiH concentration of 1600 ppm (20 DP) determined via FT-IR. The flask was heated to 70° C., and 1% solution of Karstedt's catalyst in isopropanol (IPA) was added (20 ppm Pt) as a catalyst. An exotherm was observed, and the reaction temperature was held at 70° C. for one hour until the [SiH] reached 1000 to 1100 ppm. The allyl terminated siloxane (84.95%; 179 DP) was then added to the reaction with 1% solution of Karstedt's catalyst in IPA (5 ppm Pt). The reaction was held at 70° C. for 2 hours. Reaction completion ([SiH]<10 ppm) was determined using FT-IR analysis. The viscosity of the final product was determined using Brookfield DV-III Ultra (CPE-52 spindle).

Example 12. Hydrosilylation of 600 DP Terminated

A three-neck round bottom flask equipped with a reflux condenser, nitrogen sweep, stirrer, temperature controller with thermocouple, and heating mantel was loaded with the endblocker prepared in Reference Example 10 (0.45 wt %) and SiH terminated siloxane (13 wt %), with a SiH concentration of 1600 ppm (20 DP) determined via FT-IR. The flask was heated to 70° C., and 1% solution of Karstedt's catalyst in IPA was added (20 ppm Pt) as a catalyst. An exotherm was observed, and the reaction temperature was held at 70 C for one hour until the [SiH] reached approximately 1200 ppm. The allyl terminated siloxane (86.55 wt %; 179 DP) was then added to the reaction with 1% solution of Karstedt's catalyst in IPA (5 ppm Pt). The reaction was held at 70° C. for 2 hours. Reaction completion ([SiH].<10 ppm) was determined using FT-IR analysis. The viscosity of the final product was determined using Brookfield DV-III Ultra (CPE-52 spindle).

Example 13. Hydrosilylation of 1000 DP Terminated

A three-neck round bottom flask equipped with a reflux condenser, nitrogen sweep, stirrer, temperature controller with thermocouple, and heating mantel was loaded with the endblocker prepared in Reference Example 10 (0.27 wt %) and SiH terminated siloxane (11.85 wt %), with a SiH concentration of 1600 ppm (20 DP) determined via FT-IR. The flask was heated to 70° C., and 1% solution of Karstedt's catalyst in IPA was added (20 ppm Pt) as a catalyst. An exotherm was observed, and the reaction temperature was held at 70° C. for one hour until the [SiH] reached 1300 ppm. The allyl terminated siloxane (87.88 wt %; 179 DP) was then added to the reaction with 1% solution of Karstedt's catalyst in IPA (5 ppm Pt). The reaction was held at 70° C. for 2 hours. Reaction completion ([SiH]<10 ppm) was determined using FT-IR analysis. The viscosity of the final product was determined using Brookfield DV-III Ultra (CPE-52 spindle).

Example 14: Preparation of Emulsions (Prophetic)

The emulsification procedure will be performed on a Hauschild Speedmixer. To a plastic cup will be added the silicone block copolymer prepared in Example 11, Brig 35L surfactant, optionally lactic acid, and a first quantity of water. The mixture will be sheared at maximum speed for 20 seconds. An additional quantity of water will be added, and the emulsion will again be mixed on the Speedmixer. The amounts in each emulsion sample to be prepared are shown in Table 4, below.

TABLE 4

Emulsions

| Ingredient | Amount in Sample 14A | Amount in Sample 14B | Amount in Sample 14C | Amount in Sample 6D |
|---|---|---|---|---|
| Silicone Block Copolymer of Example 11 | 10 | 4 | 10 | 4 |
| Brig 35L Surfactant | 0.5 | 4 | 0.6 | 4 |
| Water, First Quantity + Additional Quantity | 3 + 3 | 2 + 8 | 2 + 4 | 2 + 7 |
| Lactic Acid | none | 0.1 | none | 0.06 |

Example 15: Preparation of Hair Conditioner Formulations (Prophetic)

Samples of emulsions as described in Example 14 will be added to rinse-off conditioning formulations using an amount sufficient to provide 2% the silicone block copolymer. The conditioning formulations are shown in Table 5, below. The conditioners of the present invention will be prepared using Emulsions 14A, 14B, 14C and 14D from Table 4.

TABLE 5

Conditioners

| Ingredient | Weight Percent | Weight Percent | Weight Percent | Weight Percent |
|---|---|---|---|---|
| Deionized Water | q.s. to 100% | q.s. to 100% | q.s. to 100% | q.s. to 100% |
| Hydroxyethyl-cellulose[1] | 1.5 | 1.5 | 1.5 | 1.5 |
| Cetearyl Alcohol[2] | 1.0 | 1.0 | 1.0 | 1.0 |
| PEG-100 Stearate & Glyceryl Stearate[3] | 1.0 | 1.0 | 1.0 | 1.0 |
| Emulsion 14A | 3.3 | — | — | — |
| Emulsion 14B | — | 10.0 | — | — |
| Emulsion 14C | — | — | 3.4 | — |
| Emulsion 14D | — | — | — | 9.6 |
| Phenoxyethanol (and) Ethylhexylglycerin[4] | 0.2 | 0.2 | 0.2 | 0.2 |

[1]CELLOSIZE™ PCG-10 available Dow Chemical of Midland, MI
[2]Crodocol CS-50® available from Croda Inc. of Edison, NJ
[3]Arlacel® 165 available from Uniqema of Wilmington, DE
[4]Euxyl® PE 9010 available from Schülke & Mayr Example 16—Conditioning Shampoo Formulations (Prophetic)

Samples of emulsions described in Example 14 will be added to shampoo formulations in an amount sufficient to provide 2% of the silicone block copolymer. The shampoo formulations are shown in Table 6. The shampoos of the present invention will be prepared using A, B, C and D emulsions from Table 4.

TABLE 6

Conditioning Shampoos

| Ingredient | Weight % | Weight % | Weight % | Weight % |
|---|---|---|---|---|
| Deionized Water | q.s. to 100% | q.s. to 100% | q.s. to 100% | q.s. to 100% |
| Sodium Lauryl Ether Sulfate[1] | 30 2.0 | 30 | 30 | 30 |
| Cocamide MIPA[2] | 2.0 | 2.0 | 2.0 | 2.0 |
| Cocamidopropyl Betaine[3] | 7.0 | 7.0 | 7.0 | 7.0 |
| Polyquaternium-10[4] | 0.3 | 0.3 | 0.3 | 0.3 |
| PEG-150 Pentaerythrityl Tetrastearate[5] | 1.5 | 1.5 | 1.5 | 1.5 |
| Emulsion 14A | 3.3 | — | — | — |
| Emulsion 14B | — | 10.0 | — | — |
| Emulsion 14C | — | — | 3.4 | — |
| Emulsion 14D | — | — | — | 9.6 |
| Phenoxyethanol (and) Ethylhexylglycerin[6] | 0.4 | 0.4 | 0.4 | 0.4 |

[1]Rhodapex® ESC-3/A2 available from Solvay Novecare
[2]Monamid 705® available from Uniqema of New Castle, DE
[3]Monateric CAB-LC® available from Uniqema of New Castle, DE
[4]UCARE Polymer JR-30M available from Dow/Amerchol of Midland, MI
[5]Crothix® available from Croda Inc. of Edison, NJ
[6]Euxyl® PE 9010 available from Schülke & Mayr Deionized water is added to the mixing vessel. In order to keep the silicone block copolymer loading constant throughout testing, it is necessary to adjust the water level added depending on the percent silicone block copolymer in the various emulsions used. With moderate agitation, the polyquaternium-10 is dispersed until fully dissolved. This is then heated to 75° C. and the PEG-150 pentaerythrityl tetrastearate is added with continual mixing. Heat is decreased to 40° C. and sodium lauryl ether sulfate, cocamide MIPA, cocamidopropyl betaine are added in that order. When completely incorporated, the silicone block copolymer emulsion is added to the base shampoo. The shampoo is mixed for 5-10 minutes and then Phenoxyethanol (and) Ethylhexylglycerin is added. The water loss is compensated for and the formulation is mixed for an additional 5 minutes. The final pH of the shampoo formulations are approximately 5.5-6.0.

Example 17—Leave-On Conditioner Application (Prophetic)

The emulsions described in Example 14 will be further diluted with water to a 2% concentration of silicone block copolymer.

Example 18—Sulfate-Free Shampoo (Prophetic)

Samples of emulsions described in Example 6 and Example 14 will be added to sulfate-free shampoo formulations in an amount sufficient to provide 2% of the silicone block copolymer. The shampoo formulations are shown in Table 7. The shampoos of the present invention will be prepared using A, B, C and D emulsions from Table 4. The shampoos are prepared by mixing the ingredients of Phase A and heating to 70° C. to 75° C. The ingredients of Phase B are mixed and the resulting mixture added to Phase A. The resulting mixture of Phase A and Phase B will be cooled to RT. The ingredients of Phase C will be mixed and then added to the mixture of Phase A and Phase B.

TABLE 7

| Phase | Ingredient | Weight % | Weight % | Weight % | Weight % | Weight % | Weight % |
|---|---|---|---|---|---|---|---|
| Phase A | Deionized Water | q.s to 10% | q.s. to 100% | q.s. to 100% | q.s. to 100% | q.s. to 100% | q.s. to 100% |
| | Polyquaternium-10[1] | 0.3 | 0.3 | 0.3 | 0.3 | 0.3 | 0.3 |
| Phase B | Decyl Glucoside[2] | 8.0 | 8.0 | 8.0 | 8.0 | 8.0 | 8.0 |
| | Cocamidopropyl Betaine[3] | 16.0 | 16.0 | 16.0 | 16.0 | 16.0 | 16.0 |
| | Sodium Lauroyl Sacrosinate[4] | 5.0 | 5.0 | 5.0 | 5.0 | 5.0 | 5.0 |
| | PEG-150 Pentaerythrityl Tetrastearate[5] | 2.3 | 2.3 | 2.3 | 2.3 | 2.3 | 2.3 |
| Phase C | Emulsion 14A | 3.3 | — | — | — | — | — |
| | Emulsion 14B | — | 10.0 | — | — | — | — |
| | Emulsion 14C | — | — | 3.4 | — | — | — |
| | Emulsion 14D | — | — | — | 9.6 | — | — |
| | Emulsion 6A | — | — | — | — | 3.3 | — |
| | Emulsion 6B | — | — | — | — | — | 3.3 |
| | Phenoxyethanol and Methylisothiazolinone[6] | 0.5 | 0.5 | 0.5 | 0.5 | 0.5 | 0.5 |

[1] UCARE Polymer JR-30M available from Dow Chemical of Midland, MI
[2] EcoSense™ 3000 available from Dow Chemical of Midland, MI
[3] Mirataine C-30 available from Rhodia
[4] Crodasinic LS 30 available from Croda Inc. of Edison, NJ
[5] Crothix ® available from Croda Inc. of Edison, NJ
[6] Neolone PE available from Dow Chemical of Midland, MI Example 19—Leave in Conditioner Cream (Prophetic)

A leave in conditioner cream will be prepared by combining the ingredients in Table 8, as follows:
1. Heat ingredient 1 to 70° C.
2. Disperse ingredient 2 into ingredient 1 and mix until homogeneous.
3. Add ingredient 3 with gentle mixing.
4. In a separate vessel, combine phase B ingredients and mix.
5. Heat phase B ingredients at 70° C.
6. Mix phase B ingredients together until homogeneous.
7. Add phase A to phase B in increments and stir while keeping phase B warm enough to keep the wax melted. Stir until homogeneous.
8. Cool to room temperature while gently mixing.
9. Add phase C ingredients in order listed, mixing well after each addition.
10. Adjust pH to 4 with citric acid solution.

TABLE 8

| Phase | Ingredient | Weight % | Weight % | Weight % | Weight % | Weight % | Weight % |
|---|---|---|---|---|---|---|---|
| A | 1. Water | q.s. to 100% | q.s. to 100% | q.s. to 100% | q.s. to 100% | q.s. to 100% | q.s. to 100% |
| | 2. Hydroxyethylcellulose | 1.5 | 1.5 | 1.5 | 1.5 | 1.5 | 1.5 |
| | 3. Glycerin | 5 | 5 | 5 | 5 | 5 | 5 |
| B | 4. Behentrimonium Methosulfate (and) Cetearyl Alcohol | 3 | 3 | 3 | 3 | 3 | 3 |
| | 5. C10-40 Isoalkylamidopropylethyldimonium Ethosulfate and Dipropylene Glycol | 2.5 | 2.5 | 2.5 | 2.5 | 2.5 | 2.5 |
| | 6. Jojoba Oil | 1 | 1 | 1 | 1 | 1 | 1 |
| | 7. Cetyl Alcohol | 0.3 | 0.3 | 0.3 | 0.3 | 0.3 | 0.3 |
| C | 8. Hydrolyzed Wheat Gluten | 0.05 | 0.05 | 0.05 | 0.05 | 0.05 | 0.05 |
| | 9. Panthenol | 0.1 | 0.1 | 0.1 | 0.1 | 0.1 | 0.1 |
| | Emulsion 14A | 5.36 | 0 | 0 | 0 | 0 | 0 |
| | Emulsion 14B | 0 | 5.36 | 0 | 0 | 0 | 0 |
| | Emulsion 14C | 0 | 0 | 5.36 | 0 | 0 | 0 |
| | Emulsion 14D | 0 | 0 | 0 | 5.36 | 0 | 0 |
| | Emulsion 6A | 0 | 0 | 0 | 0 | 5.36 | 0 |
| | Emulsion 6B | 0 | 0 | 0 | 0 | 0 | 5.36 |
| | 11. Water (and) Heliantus Annuus Seed Oil (and) Glycerin (and) Bambusa Vulgaris Extract (and) Sclerotium Gum (and) Tocopherol | 1 | 1 | 1 | 1 | 1 | 1 |
| | 12. Phenoxyethanol and Methylisothiazolinone | 0.5 | 0.5 | 0.5 | 0.5 | 0.5 | 0.5 |

Example 20—Preparation of an Endblocker

A 500 mL three neck round bottom flask was equipped with a mechanical mixer, thermocouple, heating mantle, condenser, and addition funnel. Glycidol (111.16 g) was added to the flask with toluene. (148.81 g) and mixed, resulting in a hazy solution. Allylamine (39.0 g) was added dropwise to the reaction mixture via addition funnel. The addition rate to control the reaction temperature at approximately 35° C. The reaction flask was allowed to stir overnight. Using a common distillation column, the material was stripped at 140° C. for 4 hours to remove toluene and other volatiles. Reaction completion was confirmed using 13C-NMR where the epoxy peaks at 44 and 52 ppm from the glycidol have disappeared in the final product.

Example 21—Preparation of Silicone Block Copolymers

Examples 2, 3, and 4 were repeated. Samples of silicone block copolymers were produced, and viscosity of each was evaluated as described above. A summary is in Table 9, below.

TABLE 9

Silicone Block Copolymers

| Example | Copolymer | DP | Viscosity (cP) |
|---|---|---|---|
| 2 | A | 400 | 9000-13000 |
| 3 | B | 600 | 16000-23000 |
| 4 | C | 1000 | 30000-34000 |

Example 22—Rinse-Off Conditioner

Rinse-off conditioner samples were prepared using the ingredients shown below in Table 10.

TABLE 10

Rinse-off Conditioners

| Ingredient | Control[5] Weight % | Copolymer A from Example 21 Weight % | Copolymer C from Example 21 Weight % | 8500 Conditioning Agent[7] Weight % |
|---|---|---|---|---|
| Deionized Water | 95.8 | 94.8 | 94.8 | 94.8 |
| Hydroxyethylcellulose[1] | 1.5 | 1.5 | 1.5 | 1.5 |
| Tetrasodium EDTA[2] | 0.2 | 0.2 | 0.2 | 0.2 |
| Cetearyl Alcohol[3] | 1.0 | 1.0 | 1.0 | 1.0 |
| PEG-100 Stearate & Glyceryl Stearate[4] | 1.0 | 1.0 | 1.0 | 1.0 |
| Copolymer | 0 | 1.0 | 1.0 | 1.0 |
| Phenoxyethanol and Methylisothiazolinone[6] | 0.5 | 0.5 | 0.5 | 0.5 |

[1]CELLOSIZE™ PCG-10 available Dow Chemical
[2]VERSENE™ 220 available Dow Chemical
[3]Crodacol™ CS50 available from Croda
[4]Arlacel™ 165 available from Croda
[5]Control contains no silicone block copolymer
[6]NEOLONE™ PE available from Dow Chemical
[7]8500 Conditioning Agent available from Dow Corning Corporation Deionized water was added to a mixing vessel and heated to 70° C. With moderate agitation, the hydroxyethyl cellulose was dispersed until fully dissolved. Heat was decreased to 60° C. and cetearyl alcohol and PEG-100 stearate and glyceryl stearate and silicone block copolymer (if any) were added. The conditioner was mixed for 3 minutes and then tetrasodium EDTA was added and mixed for 3 minutes. When the temperature was below 40° C., the phenoxyethanol and methylisothiazolinone were added. The water loss was compensated for and the resulting formulation was mixed for an additional 5 minutes. The final pH of the conditioner formulations were all approximately 5.

Medium bleached European human hair from International Hair Importers was used for testing the conditioners prepared herein. Each tress weighed 2 grams. Each tress was rinsed for 15 seconds under a stream of 40° C. tap water. Using a pipette, 0.4 grams of a solution containing nine percent of sodium lauryl sulfate was applied and lathered through the tress for 30 seconds. The tress was rinsed for 30 seconds under running water. Excess water was removed from the tress by passing the tress between the index and middle fingers of the hand. The tresses were placed on a tray covered with paper towels and dried overnight. Each tress was hand combed three times with the narrow teeth of an ACE® comb, and evaluated using INSTRON WET and INSTRON DRY COMBING procedures. INSTRON procedures are standard, recognized, and industrially acceptable protocols, see for example, U.S. Pat. No. 5,389,364 (Feb. 14, 1995), U.S. Pat. No. 5,409,695 (Apr. 25, 1995), U.S. Pat. No. 5,419,627 (May 30, 1995), and U.S. Pat. No. 5,504,149 (Apr. 2, 1996).

For tests involving conditioners, hair tresses were rinsed with tap water for 30 seconds at 40° C. The test conditioner was applied to the tress in the amount of 0.8 grams, and the tress was stroked for 30 seconds. The tress was rinsed for 30 seconds under tap water at 40° C. Excess water was removed by pulling the tress through the index and middle fingers of the hand. The tresses were allowed to dry separately on a paper towel overnight at room temperature. The tresses were combed once before performing an INSTRON study.

INSTRON COMBING was used for determining conditioning performance by the ease of wet combing and the ease of dry combing. The test employed an INSTRON strain gauge, which was equipped to measure the force required to comb the hair. The conditioning performance was based on the ability of a particular hair treatment formulation, such as a shampoo or a hair conditioner, to reduce the force required to comb the hair with the INSTRON strain gauge. The force was reported as an Average Combing Load (ACL). The lower the number of the ACL value, the better was the conditioning effect imparted by the formulation being tested. Typically, ACL baselines were initially established using untreated tresses that have only been washed with a sodium lauryl sulfate solution. The effectiveness of a treatment was then expressed as an ACL of the treated tress or percent reduction in ACL, calculated using the relationship:

$$(\text{untreated hair ACL} - \text{treated hair ACL}) \times 100 \text{ divided by the untreated hair ACL}$$

According to the INSTRON WET COMBING method, hair was first wetted by dipping it into distilled water, and then the hair was detangled by combing the tress three times. The tress was then retangled by dipping in distilled water three times. Excess water was removed by passing the tress through the index and middle fingers of the hand twice. The tress was placed on a hanger and INSTRON combed. Retangling and INSTRON combing were repeated until all data points are collected. An average combing force of three tresses was measured for each treatment.

According to the INSTRON DRY COMBING method, hair was detangled by combing the tress 3 times. Then hair was retangled by swirling the tress clockwise 3 times and swirling it counter clockwise 3 times. The tress was then placed on a hanger and INSTRON combed. Retangle and Instron combing were repeated until all data points were collected. An average combing force for three tresses was measured for each treatment.

The results of INSTRON WET COMBING using conditioners from Table 10 are shown in Table 11. The results show that the silicone block copolymers having an aminofunctional endblocking group containing rinse-off conditioners of the present invention provided an improvement in the reduction in wet combing force compared to the control conditioner without silicone and were similar in performance to the conditioner containing DOW CORNING® 8500 Conditioning Agent, which is an amino glycol silicone copolymer. The conditioners containing the silicone block copolymers having an aminofunctional endblocking group of the present invention are therefore capable of significantly improving the wet conditioning properties of hair under the conditions tested in these examples.

The results of INSTRON DRY COMBING using conditioners from Table 10 are shown in Table 11. The results show that rinse-off conditioners containing the silicone block copolymers having an aminofunctional endblocking group of the present invention provided an improvement in the reduction in dry combing force compared to the control conditioner without a copolymer and were similar in performance to the conditioner containing DOW CORNING® 8500 Conditioning Agent. The conditioners containing the silicone block copolymers having an amino functional endblocking group of the present invention are therefore capable of significantly improving the dry conditioning properties of hair under the conditions tested in these examples.

TABLE 11

| Sample | % Wet Reduction | % Dry Reduction |
| --- | --- | --- |
| Control | 4 | 64 |
| Copolymer A from Example 21 | 94 | 91 |
| Copolymer C from Example 21 | 93 | 85 |
| 8500 Conditioning Agent | 97 | 87 |

COEFFICIENT OF FRICTION is an industry standard method for measuring reduced frictional properties of treatments on hair and correlates with sensory attributes for smoothness and softness. A Diastron MTT175 tensile tester with 150 g normal force mounted on rubber probe was used for testing in a temperature and humidity controlled room. Three tresses per treatment and 5 measurements per tress were tested to generate the friction data both with and against the hair cuticles. Coefficient of friction (COF)=F/N, where F was the externally applied force and N was the normal force. The same tresses from the combing study were used for measuring the coefficient of friction in the dry state.

The results of COEFFICIENT OF FRICTION using conditioners from Table 10 are shown in Table 12. The results show that rinse-off conditioners containing silicone block copolymers having an aminofunctional endblocking group of the present invention provided an improvement for reduced friction compared to the control conditioner without a copolymer and to the conditioner containing the DOW CORNING® 8500 Conditioning Agent. The conditioners containing the silicone block copolymers having an aminofunctional endblocking group of the present invention are therefore capable of significantly reducing the dry frictional properties of hair under the conditions tested in these examples.

TABLE 12

| Sample | COF with cuticle | COF against cuticle |
| --- | --- | --- |
| Control | 0.83 | 1.43 |
| Polymer A fromExample 21 | 0.14 | 0.45 |
| Polymer C fromExample 21 | 0.16 | 0.41 |
| 8500 Conditioning Agent | 0.24 | 0.68 |

The treatment of damaged hair with a silicone-containing conditioner can provide a protective film on the surface of the hair fibers to increase the HYDROPHOBICITY compared to untreated, damaged hair, which is more hydrophilic. Maintaining the hydrophobicity that can last through washing is a desired performance benefit. To measure long lasting hydrophobicity several droplets of water were placed on the tresses treated with the conditioners from Table 2, ensuring the hair fibers were combed straight and the tresses were held tightly on both ends with a holder. After washing 1, 5 and 10 times with a commercial non-silicone containing shampoo pictures were taken after the drops were initially placed on the tress and again after 5 minutes to determine if the water droplets remained or absorbed into the hair.

The results from the long lasting HYDROPHOBICITY test show the water droplets placed on the tresses treated with the control conditioner without silicone absorb immediately after washing one time with the shampoo while the water droplets placed on the tresses treated with the conditioners containing the silicone block copolymers having an aminofunctional endblocking group and those treated with DOW CORNING® 8500 Conditioning Agent remained for at least 5 minutes before washing and after washing 1 and 5 times. The droplets also remained for at least 1 minute on the tresses washed 10 times with the shampoo. The conditioners containing the silicone block copolymers having an aminofunctional endblocking group of the present invention are therefore capable of providing long lasting hydrophobicity of damaged hair.

Example 23—Conditioning Shampoos

Conditioning shampoo samples were prepared using the ingredients shown below in Table 13.

TABLE 13

| | Conditioning Shampoo Samples | | | |
| --- | --- | --- | --- | --- |
| Ingredient | Control[7] Weight % | Copolymer A from Example 21 Weight % | Copolymer C from Example 21 Weight % | 8500 Conditioning Agent Weight % |
| Deionized Water | 59.75 | 59.1 | 59.1 | 58.75 |
| Sodium Lauryl Ether Sulfate[1] | 30 | 30 | 30 | 30 |
| Polyquaternium-10[2] | 0.3 | 0.3 | 0.3 | 0.3 |
| Tetrasodium EDTA[3] | 0.2 | 0.2 | 0.2 | 0.2 |
| PEG-150 Pentaerythrityl Tetrastearate[4] | 1.25 | 0.9 | 0.9 | 1.25 |
| Cocamide MEA[5] | 1 | 1 | 1 | 1 |
| Cocamidopropyl Betaine[6] (30% active) | 7 | 7 | 7 | 7 |

TABLE 13-continued

Conditioning Shampoo Samples

| Ingredient | Control[7] Weight % | Copolymer A from Example 21 Weight % | Copolymer C from Example 21 Weight % | 8500 Conditioning Agent Weight % |
|---|---|---|---|---|
| Copolymer | 0 | 1 | 1 | 1 |
| Phenoxyethanol and Methylisothiazolinone[8] | 0.5 | 0.5 | 0.5 | 0.5 |

[1]Rhodapex® ESC-3/A2 available from Solvay Novecare
[2]UCARE™ Polymer JR-30M available from Dow Chemical
[3]VERSENE™ 220 available Dow Chemical
[4]Crothix™ PA-(MH) available from Croda
[5]Incromide™ CMEA available from Croda
[6]Mackam® C-37 available from Glenn Corp.
[7]The control did not contain a copolymer.
[8]NEOLONE™ PE available from Dow Chemical
9. 8500 Condition Agent available from Dow Corning Corporation.

Conditioning shampoo samples were prepared as follows. With moderate agitation, the sodium lauryl ether sulfate and water were combined. Then the polyquaternium-10 was dissolved into the solution while heating. The tetrasodium EDTA was added and mixed until dissolved. The resulting mixture was heated to 75° C., and the PEG-150 pentaerythrityl tetrastearate and cocamide MEA were added and mixing continued for 10 minutes. Heat was decreased, and cocamidopropyl betaine was added. When completely incorporated, the copolymer (if present) was added to this base shampoo and mixed for 5-10 minutes. When temperature reached 40° C., the phenoxyethanol and methylisothiazolinone were added. The water loss was compensated for, and the formulation was mixed for an additional 10 minutes. The final pH of the shampoo formulations were approximately 5-6.

Medium bleached European human hair from International Hair Importers was used for testing the conditioning shampoos prepared as described above. Each tress weighed 2 grams. Each tress was rinsed for 15 seconds under a stream of 40° C. tap water. Using a pipette, 0.4 grams of a solution containing nine percent of sodium lauryl sulfate was applied and lathered through the tress for 30 seconds. The tress was rinsed for 30 seconds under running water. Excess water was removed from the tress by passing the tress between the index and middle fingers of the hand. The tresses were placed on a tray covered with paper towels and dried overnight. Each tress was hand combed three times with the narrow teeth of an ACE® comb, and evaluated using INSTRON WET and INSTRON DRY COMBING procedures, as described above.

For tests involving shampoos, hair tresses were rinsed with tap water for 30 seconds at 40° C. The test shampoo was applied to the tress in the amount of 0.8 grams, and the tress was stroked for 30 seconds. The tress was rinsed for 30 seconds under tap water at 40° C. Excess water was removed by pulling the tress through the index and middle fingers of the hand. The tresses were allowed to dry separately on a paper towel overnight at room temperature. The tresses were combed once before performing an INSTRON study.

The results of INSTRON WET COMBING using shampoos from Table 13 are shown in Table 14. The results show that the silicone block copolymers having an aminofunctional endblocking group containing shampoos of the present invention provided an improvement in the reduction in wet combing force compared to the control shampoo without silicone and were similar in performance to the DOW CORNING® 8500 Conditioning Agent containing shampoo. The shampoos containing the silicone block copolymers having an aminofunctional endblocking group of the present invention are therefore capable of significantly improving the wet conditioning properties of hair.

The results of INSTRON DRY COMBING using shampoos from Table 13 are shown in Table 14. The results show that the shampoos containing silicone block copolymers having an aminofunctional endblocking group of the present invention provided an improvement in the reduction in dry combing force compared to the control shampoo without copolymer and were similar in performance to the shampoo containing DOW CORNING® 8500 Conditioning Agent. The shampoos containing the silicone block copolymers having an aminofunctional endblocking group of the present invention were therefore capable of significantly improving the dry conditioning properties of hair under the conditions of this example.

TABLE 14

| Sample | % Wet Reduction | % Dry Reduction |
|---|---|---|
| Control | 50 | 46 |
| Polymer A | 78 | 79 |
| Polymer C | 80 | 79 |
| 8500 Conditioning Agent | 77 | 71 |

The results of COEFFICIENT OF FRICTION using shampoos from Table 13 are shown in Table 15. The results show that shampoos containing silicone block copolymers having an aminofunctional endblocking group of the present invention provided an improvement for reduced friction compared to the control shampoo without copolymer and to the shampoo containing DOW CORNING® 8500 Conditioning Agent. The shampoos containing the silicone block copolymers having an aminofunctional endblocking group of the present invention were therefore capable of significantly reducing the dry frictional properties of hair under the conditions of this example.

TABLE 15

| Sample | COF with cuticle | COF against cuticle |
|---|---|---|
| Control | 0.81 | 1.48 |
| Polymer A | 0.45 | 1.20 |
| Polymer C | 0.45 | 1.21 |
| 8500 Conditioning Agent | 0.75 | 1.52 |

Without wishing to be bound by theory, it is thought that the present invention may provide a cost effective silicone block copolymer having an amine functional group. Without wishing to be bound by theory, it is thought that the silicone block copolymer having an amine functional group may provide one or more benefits in hair care compositions, e.g., increased shine, volumization, moisturization, color retention, and/or heat protection; conditioning benefits, including wet and dry combing and smooth feeling; reducing drying time, reducing static, and/or styling benefits such as curl retention, hair alignment, and/or frizz reduction; and/or hair protection such as resistance to breakage, hydrophoicity, targeted deposition, resistance to split ends and/or repair of split ends.

All amounts, ratios, and percentages are by weight unless otherwise indicated. The articles 'a', 'an', and 'the' each refer to one or more, unless otherwise indicated. The disclosure of ranges includes the range itself and also anything subsumed therein, as well as endpoints. For example, disclosure of a range of 2.0 to 4.0 includes not only the range of 2.0 to 4.0, but also 2.1, 2.3, 3.4, 3.5, and 4.0 individually, as well as any other number subsumed in the range. Furthermore, disclosure of a range of, for example, 2.0 to 4.0 includes the subsets of, for example, 2.1 to 3.5, 2.3 to 3.4, 2.6 to 3.7, and 3.8 to 4.0, as well as any other subset subsumed in the range. Similarly, the disclosure of Markush groups includes the entire group and also any individual members and subgroups subsumed therein. For example, disclosure of the Markush group a hydrogen atom, an alkyl group, an aryl group, or an aralkyl group includes the member alkyl individually; the subgroup alkyl and aryl; and any other individual member and subgroup subsumed therein.

Abbreviations used herein are defined as follows. The abbreviation "cm$^2$" means square centimeters. The abbreviation "cP" means centiPoise. The abbreviation "g" means grams. "DP" means the degree of polymerization. "FT-IR" means Fourier Transfer Infrared. "GPC" means gel permeation chromatography. The abbreviation "mg" means milligrams. "Mn" means number average molecular weight. Mn may be measured using GPC. The abbreviation "mPa·s" means milliPascal seconds. "Mw" means weight average molecular weight. "NMR" means nuclear magnetic resonance. The abbreviation "ppm" means parts per million. RT means room temperature of 25° C.

The invention claimed is:

1. A silicone block copolymer having an aminofunctional endblocking group, or a quat thereof, has average formula:

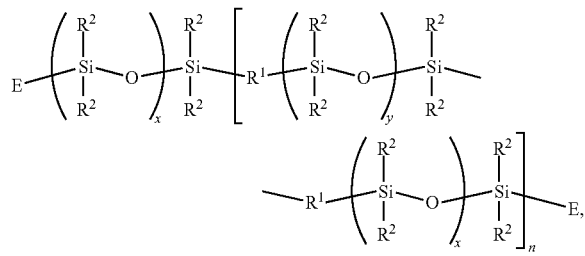

where
each subscript x is independently >0,
each subscript y is independently >0,
subscript n is ≥1,
each R$^1$ is independently a divalent organic group free of polyoxyalkylene, and
each R$^2$ is independently a monovalent hydrocarbon group or a monovalent halogenated hydrocarbon group;
at least one E is an aminofunctional endblocking group or a quat thereof, or both instances of E are aminofunctional endblocking groups or quats thereof, where the aminofunctional endblocking group has a formula selected from

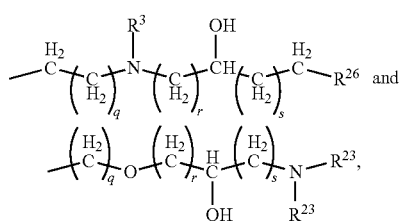

where
subscript q is ≥0,
subscript r is >0,
subscript s is ≥0, and
R$^3$ is independently H, alkyl, or a group of formula

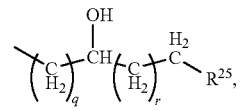

each R$^{25}$ is independently H or OH and
each R$^{23}$ is independently an alkyl group or a hydroxyalkyl group,
with the proviso that when only one instance of E is aminofunctional, then the other instance of E is a monovalent organic group selected from the group consisting of a monovalent hydrocarbon group, a monovalent halogenated hydrocarbon group, or a polyoxyalkylene group.

2. The silicone block copolymer of claim 1, where one instance of E is the aminofunctional endblocking group or a quat thereof, and another instance of E is a monovalent hydrocarbon group, a monovalent halogenated hydrocarbon group, or a polyoxyalkylene group.

3. An emulsion comprising:
(1) the silicone block copolymer of claim 1,
(2) water, and
(3) a surfactant.

4. A method for treating a substrate selected from textiles and leather comprising:
(A) applying to the substrate, a treatment composition comprising the silicone block copolymer of claim 1, and
(B) drying the substrate.

5. A personal care composition comprising:
(1) the silicone block copolymer of claim 1, and
(2) a carrier that permits application.

6. A shampoo comprising:
(1) the silicone block copolymer of claim 1,
(2) water, and
(3) an anionic surfactant and/or an amphoteric surfactant,
optionally (4) a preservative, and
optionally (5) a cationic deposition polymer, and
optionally (6) a thickener.

7. A hair conditioner comprising:
(A) the silicone block copolymer of claim 1,
(B) water,
optionally (C) a thickener,
(D) a fatty alcohol,
optionally (E) other emulsifiers,
optionally (F) a preservative, and
optionally (G) a cationic deposition polymer.

8. An emulsion comprising:
(1) the silicone block copolymer of claim 2,
(2) water, and
(3) a surfactant.

9. A method for treating a substrate selected from textiles and leather comprising:
(A) applying to the substrate, a treatment composition comprising the silicone block copolymer of claim 2, and
(B) drying the substrate.

10. A method for treating a substrate selected from textiles and leather comprising:

(A) applying to the substrate, a treatment composition comprising the emulsion of claim 3, and
(B) drying the substrate.

11. A personal care composition comprising:
(1) the emulsion of claim 3, and
(2) a carrier that permits application.

12. A shampoo comprising:
(1) the emulsion of claim 3,
(2) water, and
(3) an anionic surfactant and/or an amphoteric surfactant,
optionally (4) a preservative, and
optionally (5) a cationic deposition polymer, and
optionally (6) a thickener.

13. A hair conditioner comprising:
(A) the emulsion of claim 3,
(B) water,
optionally (C) a thickener,
(D) a fatty alcohol,
optionally (E) other emulsifiers,
optionally (F) a preservative, and
optionally (G) a cationic deposition polymer.

* * * * *